United States Patent
Abbosh et al.

(10) Patent No.: US 11,551,386 B2
(45) Date of Patent: Jan. 10, 2023

(54) TOMOGRAPHIC IMAGING SYSTEM AND PROCESS

(71) Applicant: EMvision Medical Devices Ltd, Brisbane (AU)

(72) Inventors: Amin Abbosh, St. Lucia (AU); Ali Zamani, St. Lucia (AU); Arman Afsari, St. Lucia (AU)

(73) Assignee: EMvision Medical Devices Ltd, Brisbane (AU)

( * ) Notice: Subject to any disclaimer, the term of this patent is extended or adjusted under 35 U.S.C. 154(b) by 0 days.

(21) Appl. No.: 16/620,430

(22) PCT Filed: May 9, 2018

(86) PCT No.: PCT/AU2018/050425
§ 371 (c)(1),
(2) Date: Dec. 6, 2019

(87) PCT Pub. No.: WO2018/223178
PCT Pub. Date: Dec. 13, 2018

(65) Prior Publication Data
US 2021/0082160 A1 Mar. 18, 2021

(30) Foreign Application Priority Data
Jun. 8, 2017 (AU) .................................. 2017902192

(51) Int. Cl.
*G06T 11/00* (2006.01)
*A61B 6/03* (2006.01)
(52) U.S. Cl.
CPC .............. *G06T 11/003* (2013.01); *A61B 6/03* (2013.01)

(58) Field of Classification Search
CPC ....... G06T 11/003; G06T 11/006; A61B 6/03; A61N 2/006; A61N 2/002; A61N 2/02; G06N 20/00; G16H 40/67
See application file for complete search history.

(56) References Cited

U.S. PATENT DOCUMENTS

| 7,239,731 B1 | 7/2007 | Semenov | |
|---|---|---|---|
| 2007/0015993 A1* | 1/2007 | Ciocan | A61B 5/0035 600/407 |

(Continued)

FOREIGN PATENT DOCUMENTS

| JP | 2017-038860 A | 2/2017 |
|---|---|---|
| WO | 2018/098387 A1 | 5/2018 |

OTHER PUBLICATIONS

Bermani et al., "An Inverse Scattering Approach Based on a Neural Network Technique for the Detection of Dielectric Cylinders Buried in a Lossy Halfspace", Progress in Electromagnetic Research, PIER, 26, p. 67-87, 2000.

(Continued)

*Primary Examiner* — David P Porta
*Assistant Examiner* — Mamadou Faye
(74) *Attorney, Agent, or Firm* — Knobbe, Martens, Olson & Bear, LLP

(57) ABSTRACT

A tomographic imaging system, including a data processing component having a memory and at least one processor configured to:
access scattering parameter data representing electromagnetic waves scattered by features within an object and originating from a plurality of antennas disposed around the object on a boundary S;

(Continued)

a) the 3D imaged domain b) 2D cross section at $z=0$ process the scattering parameter data to generate a reconstructed image representing a spatial distribution of features within the object, said processing including:

solving an electromagnetic inverse problem, wherein forward and inverse steps of the inverse problem are represented and solved as respective differential equations involving an electric field to determine values for the electric field; and process the determined values of the electric field to generate reconstructed image data representing one or more spatial distributions of one or more electromagnetic properties within the object.

18 Claims, 20 Drawing Sheets

(56) References Cited

U.S. PATENT DOCUMENTS

| | | | |
|---|---|---|---|
| 2011/0227586 A1* | 9/2011 | Lovetri | A61B 5/0507 324/637 |
| 2012/0083690 A1 | 4/2012 | Semenov | |
| 2014/0276030 A1 | 1/2014 | McCoy | |
| 2014/0276012 A1 | 9/2014 | Semenov | |

OTHER PUBLICATIONS

Bulyshev et al., "Three-dimensional vector microwave tomography: theory and computational experiments", Inverse Problems 20, p. 1239-1259, (2004).

Monsefi et al., "Direct and Inverse Computational Methods for Electromagnetic Scattering in Biological Diagnostics", published at arXiv:1312.4370vl [math-ph], p. 1-40, Dec. 16, 2013. Available at: https://arxiv.org/abs/1312.4379. Downloaded on Jun. 20, 2018.

Naseri, "Microwave Tomography for Breast Cancer Detection", MSc Thesis, Department of Signals and Systems, Division of Biomedical Engineering, Chalmers University of Technology, Sweden, 2015, p. i-69.

International Search Report issued in application No. PCT/AU2018/050425, dated Jun. 26, 2018.

Maryam Naseri: "Microwave Tomography for Breast Cancer Detection", Master's thesis Chalmers University of Technology, Aug. 17, 2015, pp. 1-53.

Farid Monsefi et al: "Direct and Inverse Computational Methods for Electromagnetic Scattering in Biological Diagnostics", Nov. 1, 2013, 61 pages.

Maryam Naseri, Microwave Tomography for Breast Cancer Detection☐Master's thesis in Master's of Biomedical Engineering, Department of Signals and Systems, Chalmers University of Technology, Sweden, 2015, pp. 1-53 https://publications.lib.chalmers.se/records/fulltext/222890/222890.pdf.

Farid Monsefi et al., Direct and Inverse Computational Methods for Electromagnetic Scattering in Biological Diagnostics, Mathematical Physics, 2013, Dec. 16, pp. 1-59, https://arxiv.org/abs/1312.4379.

* cited by examiner

TOMOGRAPHIC IMAGING SYSTEM AND PROCESS

TECHNICAL FIELD

The present invention relates to biomedical imaging, and in particular to a tomographic imaging system and process.

BACKGROUND

Inverse problems arise in electromagnetics (EM) whenever the effects of a cause are known, but the cause itself is unknown. The aim of an inverse electromagnetic problem is thus to find the EM properties of the cause according to the observed effects. By contrast, in forward problems the cause is known and the desire is to calculate the corresponding effects. In a wide range of electromagnetic inverse problems, e.g. geophysical or biomedical imaging, the cause is usually the complex permittivity (containing the relative permittivity and the conductivity) which describes an object electromagnetically, while the effects are the scattered electric fields from the object, which are detected by imaging antennas and represented by what is referred to in the art as "scattering parameters" or "S-parameters", as described in W. C. Chew, *Waves and Fields in Inhomogeneous Media*, IEEE Press, New York, 1995 ("Chew").

The main difference between forward and inverse problems is that a forward problem has a unique solution, whereas an inverse problem does not have a unique solution because the available data is insufficient to determine a unique solution.

For example, when a dipole antenna (cause) with a certain port impedance, given structure and substrate, and specific operating frequency radiates electromagnetic waves in free space, there is only one possible field distribution (effect) formed in free space by this antenna. However, if this field distribution (effect) is known and the desire is to find the properties of the antenna (cause) that has generated this field distribution, in theory an infinite number of corresponding antennas can be found.

The reconstructed images of quantitative EM inverse problems (tomography) are usually coarse and inaccurate due to diffraction effects, which are significant at microwave frequencies (unlike high frequencies such as X-Rays which propagate in straight lines). Nevertheless, these coarse images are useful as they are reconstructed from a domain non-invasively. For example, in reconstructing an image from the inside of a 'black box' (e.g., a human head, an underground mine, etc), having a coarse image representing the spatial distribution of complex permittivity within the black box is much more important than a requirement for high quantitative accuracy. This point is even more important in biomedical cases where conventional techniques such as MRI or CT-Scan are undesirably time-consuming, static and bulky, or have ionization radiation, are not portable and thus cannot be used on-site in emergency scenarios such as traffic or sport accidents or stroke where time generally has an inverse relation with the chance of survival.

In inverse problems, the permittivity over the domain of interest is always described by three-dimensional (3D) integral equations. However, as described in Chew, these equations are too complex to be solved directly, and therefore are always approximated by two-dimensional (2D) integrals to make them solvable. A two-dimensional image representing the dielectric properties of the domain is reconstructed through an iterative forward-inverse computational procedure using either Born's method, Van Den Berg's (different contrast source inversions) method, or gradient-based methods.

It is well known that these current state of the art methods for solving electromagnetic inverse problems suffer from serious limitations, including the requirements to represent the imaging antennas as ideal point sources, to assume homogeneity along one of the coordinate axes, and to use a background matching medium. These limitations restrict the reconstruction of images to two dimensions with a certain level of accuracy error, and impose manufacturing problems associated with selecting a suitable background medium with reasonable dielectric properties. Additionally, to reduce antenna mutual coupling and surface waves, a lossy matching medium is usually used. However, this also attenuates the desired signal by more than 10 dB (i.e., 90% of the useful signal will be lost), and thus the dynamic range and detection capability are significantly limited. Additionally, these methods can also be undesirably time-consuming, especially for biomedical imaging applications in emergency scenarios, such as stroke or trauma patients, where the image reconstruction time can have a dramatic effect on patient outcomes, and might even mean the difference between life and death in some instances.

It is desired, therefore, to overcome or alleviate one or more difficulties of the prior art, or to at least provide a useful alternative.

SUMMARY

In accordance with some embodiments of the present invention, there is provided a tomographic imaging process, including:
- accessing scattering parameter data representing electromagnetic waves scattered by features within an object and originating from a plurality of antennas disposed around the object on a boundary S;
- processing the scattering parameter data to generate a reconstructed image representing a spatial distribution of features within the object, said processing including:
  - solving an electromagnetic inverse problem, wherein forward and inverse steps of the inverse problem are represented and solved as respective differential equations involving an electric field to determine values for the electric field; and
  - processing the determined values of the electric field to generate reconstructed image data representing one or more spatial distributions of one or more electromagnetic properties within the object.

The inverse step may be represented by a differential equation and boundary conditions (BC) of the form:

$$(\nabla \cdot E)\varepsilon + E \cdot \nabla \varepsilon = 0$$

$$BC : \begin{cases} \varepsilon = \dfrac{\rho_s + \varepsilon_2 E_{2n}}{E_{1n}} \text{(on the imaging antennas)} \\ \varepsilon = \dfrac{\mu_0 (H_t)^2}{\omega^2 (E_{t'})^2} = \dfrac{\mu_0 (H_{t'})^2}{\omega^2 (E_t)^2} \text{ (on } S\text{)} \end{cases}$$

where $E_{1n}$ and $E_{2n}$ are the two normal components of the electric fields on both sides of the boundary S derived from the scattered field $E_n^{sct}$ recorded on S and the incident field $E_n^{inc}$ as $E_n = E_n^{inc} + E_n^{sct}$.

The forward step may be represented by a differential equation and boundary conditions (BC) of the form:

$$\nabla \times \nabla \times E - k^2 E = 0$$

$$BC: \begin{cases} n \times (E_1 - E_2) = 0 \\ n \cdot (\varepsilon_1 E_1 - \varepsilon_2 E_2) = \rho_s \\ n' \times \nabla \times E - jkn' \times E \times n' = 0 \text{ (absorbing } BC) \end{cases}$$

In some embodiments, the step of processing the scattering parameter data includes estimating permittivity values of the object by processing the scattering parameter data of the object and pre-determined training data for a plurality of different scattering media.

In some embodiments, the pre-determined training data includes regression coefficients representing a quadratic relationship between a function of scattering parameters for scattering by different training scattering media having respective different permittivity values and said respective different permittivity values.

In some embodiments, the function of scattering parameters is a variogram according to:

$$\gamma_i(h) = \frac{1}{2|N(h)|} \sum_{(j,k)\in N(h)} |S_{ij} - S_{ik}|^2$$

where h is the distance between the $j^{th}$ and $k^{th}$ transmitting antenna locations, $S_{ij}$ is the received signal at the $i^{th}$ antenna transmitted from the $j^{th}$ antenna using $N_f$ frequency samples, and N(h) denotes the set of pairs of observations ij and ik such that $|r_{ij} - r_{ik}| = h$ and $|N(h)|$ is the number of pairs in the set; and the step of estimating the permittivity values of the object includes generating a corresponding variogram from the scattering parameter data of the object.

In some embodiments, the process includes representing an effective permittivity from the view point of ith receiver $\hat{\varepsilon}_i$ as:

$$\varepsilon_i(s) = f(s)w + z(s)$$

where $s = \{\gamma, h\}$, $f(s) = [1, \gamma, h, \gamma^2, \gamma h, h\gamma, h^2]$ is a quadratic regression function vector, and w is a 7×1 vector of regression coefficients to be calculated for a minimized error z(s).

In some embodiments, the process includes energizing the plurality of antennas disposed about the object to cause the antennas to radiate electromagnetic waves onto the object.

In some embodiments, the process includes detecting the electromagnetic waves scattered by the features within the object, and generating the scattering parameter data based on said detecting.

In some embodiments, the electromagnetic waves scattered by the features within the object are detected by the antennas.

In some embodiments, the process includes determining a boundary of the object prior to the step of processing the scattering parameter data, wherein the reconstructed image is generated on the basis of the determined boundary of the object.

In some embodiments, the boundary of the object is determined from a relation between distances of the object from the antenna and corresponding reflection coefficients.

In some embodiments, the process includes determining a relation between distances of the object from the antenna and respective resonant frequencies, wherein the boundary is determined on the basis of the relation.

In some embodiments, the process includes using a vector network analyser port calibration method to determine a relation between distances of the object from the antenna and respective measurements of a scattering parameter $S_{11}$, wherein the boundary is determined on the basis of the relation.

In some embodiments, the process includes determining a relation between distances of the object from the antenna and input impedances of the antenna, wherein the boundary is determined on the basis of the relation.

In some embodiments, the process includes measuring frequency domain reflection coefficients around the object and using a frequency to time domain transform to convert the frequency domain measurements to time domain measurements, and using the geometry of the antenna to map the time domain measurements to a spatial domain to determine the boundary of the object.

In accordance with some embodiments of the present invention, there is provided a computer-readable storage medium having stored thereon processor-executable instructions that, when executed by at least one processor of a data processing system, cause the at least one processor to execute any one of the above processes.

In accordance with some embodiments of the present invention, there is provided a tomographic imaging system, including a data processing component having a memory and at least one processor configured to:

access scattering parameter data representing electromagnetic waves scattered by features within an object and originating from a plurality of antennas disposed around the object on a boundary S;

process the scattering parameter data to generate a reconstructed image representing a spatial distribution of features within the object, said processing including:

solving an electromagnetic inverse problem, wherein forward and inverse steps of the inverse problem are represented and solved as respective differential equations involving an electric field to determine values for the electric field; and process the determined values of the electric field to generate reconstructed image data representing one or more spatial distributions of one or more electromagnetic properties within the object.

The inverse step may be represented by a differential equation and boundary conditions (BC) of the form:

$$(\nabla \cdot E)\varepsilon + E \cdot \nabla \varepsilon = 0$$

$$BC: \begin{cases} \varepsilon = \dfrac{\rho_s + \varepsilon_2 E_{2n}}{E_{1n}} \text{(on the imaging antennas)} \\ \varepsilon = \dfrac{\mu_0 (H_t)^2}{\omega^2 (E_{t'})^2} = \dfrac{\mu_0 (H_{t'})^2}{\omega^2 (E_t)^2} \text{ (on } S) \end{cases}$$

where $E_{1n}$ and $E_{2n}$ are the two normal components of the electric fields on both sides of the boundary S derived from the scattered field $E_n^{sct}$ recorded on S and the incident field $E_n^{inc}$ as $E_n = E_n^{inc} + E_n^{sct}$.

The forward step may be represented by a differential equation and boundary conditions (BC) of the form:

$$\nabla \times \nabla \times E - k^2 E = 0$$

$$BC: \begin{cases} n \times (E_1 - E_2) = 0 \\ n \cdot (\varepsilon_1 E_1 - \varepsilon_2 E_2) = \rho_s \\ n' \times \nabla \times E - jkn' \times E \times n' = 0 \text{ (absorbing } BC) \end{cases}$$

In some embodiments, the at least one processor is further configured to cause the plurality of antennas disposed about the object to radiate electromagnetic waves onto the object.

The object may be a biological object. The object may be a human head. The system and process may be configured to image an injury such as a bleeding region within the brain of a patient.

Also described herein is a tomographic imaging system and process configured to image internal features of a patient, for example a human subject. The system and process may use electromagnetic radiation emitted from an antenna having a plurality of antenna elements disposed about the patient, and may be configured to rapidly generate images to identify injury to the patient. The system may be configured to image brain injuries, and may be a portable system to facilitate transport to the scene of an accident, for example, such as a road or sporting accident. The system and process may be configured to rapidly generate images of brain injuries so that such injuries can be detected quickly so that suitable treatment can be taken without undue delay.

BRIEF DESCRIPTION OF THE DRAWINGS

Some embodiments of the present invention are hereinafter described, by way of example only, with reference to the accompanying drawings, wherein.

DETAILED DESCRIPTION

In order to provide a better understanding of the context of the present invention, a more detailed account of current state-of-the-art methods for solving electromagnetic inverse problems will first be described.

Figure 1:
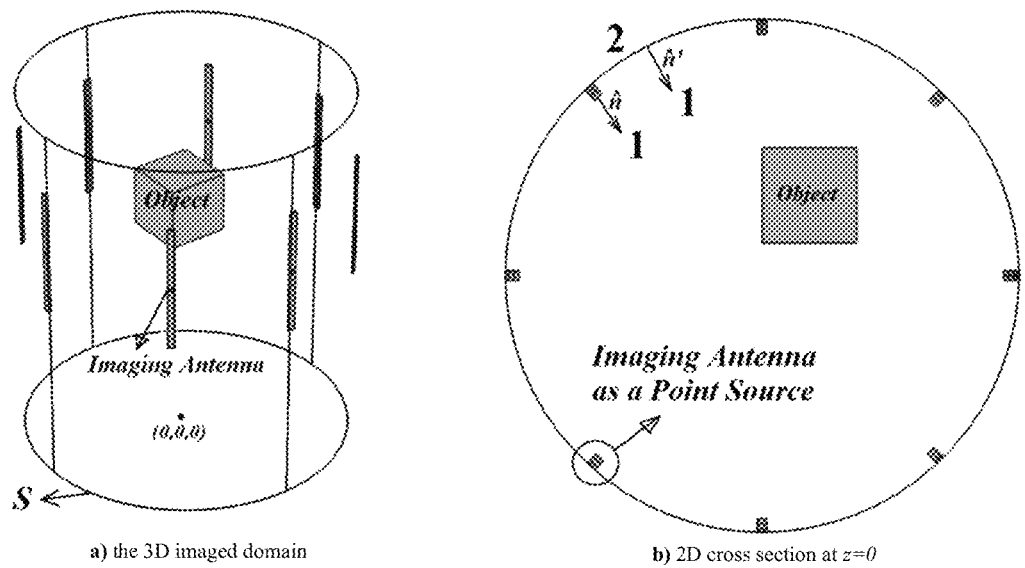
FIG. 1 includes schematic (a) oblique and (b) plan views of a microwave imaging domain (Ω), where an unknown object is imaged by imaging antennas located on a surrounding boundary S; the plan view in (b) identifies some unavoidable approximations required for integral-based inverse equations to make the equations solvable.

FIG. 1 illustrates a form of electromagnetics inverse problem wherein an incident wave ($E^{inc}$) generated by imaging antennas illuminates an unknown domain $\Omega$ and the corresponding multi-scattered signals are recorded as S-parameters on S, a surface enclosing $\Omega$ and containing the imaging antennas. The inverse problem is to generate or 'reconstruct' an image representing the spatial distribution of electromagnetic properties within the domain $\Omega$.

As known by those skilled in the art (and as described in Chew, for example), the corresponding wave propagation in the inhomogeneous medium of domain $\Omega$ is governed by the following equation and boundary conditions ("BC") in the frequency domain of the time harmonic regime, where $$\frac{\partial}{\partial t} \rightarrow j\omega$$

and $j = \sqrt{-1}$:

$$\nabla \times \nabla \times E - k^2 E = 0 \qquad (1)$$

$$BC: \begin{cases} n \times (E_1 - E_2) = 0 \\ n \cdot (\varepsilon_1 E_1 - \varepsilon_2 E_2) = \rho_s \\ n' \times \nabla \times E - jkn' \times E \times n' = 0 \text{ (absorbing } BC) \end{cases}$$

where $\rho_s$ is the surface charge on the antennas and n is the normal vector on the antenna surface. On dielectric surfaces where $\rho_s = 0$, the corresponding boundary condition reduces to $\varepsilon_1 \vec{E}_{1n} = \varepsilon_2 \vec{E}_{2n}$. In order to truncate the domain computationally, an absorbing boundary condition is applied on S (with normal vector n'). Both the normal vectors point out from the region 2 to the region 1 as seen in FIG. 1b (for n, region 2 is the internal part of the antenna). Also, $$E = E^{inc} + E^{sct} \qquad (2)$$

is the total electric field in the imaged domain $\Omega$, where $E^{inc}$ is the electric field incident on the domain, $E^{sct}$ is the scattered electric field from different objects in the domain, and k is the wavenumber defined as $k^2 = \omega^2 \mu_0 \varepsilon$, where $$\varepsilon = \varepsilon_0 \varepsilon_r + \frac{\sigma}{j\omega} \qquad (3)$$

The quantities $\varepsilon$, $\varepsilon_r$ and $\sigma$ are the complex permittivity, relative permittivity and the conductivity of the medium, and $\mu_0$, $\varepsilon_0$ and $\omega$ are the free space permeability, permittivity and angular frequency, respectively. Since in many practical problems, the unknown domain is nonmagnetic, this is assumed in the following; i.e., $\mu = \mu_0$. For simplicity, the frequency dependency of Equation (3) is neglected in the following description of the image reconstruction process, corresponding to microwave tomography at a single microwave frequency. However, this does not remove the generality of the description because the same steps can be applied at any other frequency if multi-frequency tomography is required.

In every electromagnetic inverse problem, either the complex permittivity $\varepsilon$ (which is a scalar) or the electric field E (which is a vector with three components) are unknown. The recorded $E^{sct}$ as S-parameters at the imaging antenna locations on S, and $E^{inc}$ over the domain in absence of any object, are the only available data. Having two unknowns (E is considered to be one unknown, although it has three spatial components) requires two equations to be solved, each equation for one unknown. Due to the term $k^2 \vec{E}$ in (1), where the unknowns are multiplied, the problem is generally nonlinear. Hence, assuming Equation (1) as the governing equation on E (the forward step, which indeed corresponds to three equations due to the three field components), no partial differential equation (PDE) with corresponding boundary conditions has been considered for $\varepsilon$ (as the inverse step). Consequently, the inverse problem is not solved in a PDE format due to the number of equations being insufficient.

An alternative approach in the prior art is to solve the electromagnetic inverse problems by enlisting the Green's vector identities to form the required two equations considering the object (which is generally inhomogeneous) in a homogeneous background medium. As described in Chew, these 3D integral equations are as follows:

$$\text{forward} \begin{cases} E^{inc}(p) = E(p) - k_b^2 \underbrace{\int_\Omega G(p-q)\left(\frac{\varepsilon_r(q)}{\varepsilon_b(q)} - 1\right)E(q)dq}_{\text{inductive}} \\ \quad - \underbrace{\nabla\nabla \cdot \int_\Omega G(p-q)\left(\frac{\varepsilon_r(q)}{\varepsilon_b(q)} - 1\right)E(q)dq}_{\text{galvanic}} \end{cases} \qquad (4)$$

$$\text{Inverse} \begin{cases} E^{sct}_J = k_b^2 \underbrace{\int_\Omega G(p_J-q)\left(\frac{\varepsilon_r(q)}{\varepsilon_b(q)} - 1\right)E(q)dq}_{\text{inductive}} \\ \quad + \underbrace{\nabla\nabla \cdot \int_\Omega G(p_J-q)\left(\frac{\varepsilon_r(q)}{\varepsilon_b(q)} - 1\right)E(q)dq}_{\text{galvanic}} \end{cases}$$

where $k_b$, $\varepsilon_b$ and G are the wavenumber, complex relative permittivity and the Green's function of the homogeneous background medium (which can be free space or any other homogeneous medium), q, p and $p_J$ are respectively the integral variable over the imaged domain $\Omega$, the coordinate variable, and the location of the $J^{th}$ antenna. In each equation, there are two integrals: the inductive integral corresponds to the induction current, whereas the galvanic (or voltaic) integral corresponds to the conduction current generated by the voltaic potential. The significance of this terminology is revealed by comparing (Equation 4) with the definition of the electric field in terms of the scalar and vector potentials (v and $\vec{A}$); i.e., $\vec{E} = -\nabla v - j\omega \vec{A}$, which represents the electric field as the summation of a voltaic potential (v) and a time-harmonic induction ($\vec{A}$). Comparing the above definition with Equation (4), it is apparent that the first integral term on the right-hand side of Equation (4), in the forward and inverse steps, is the inductive term corresponding to $\vec{A}$, whereas the second integral term corresponds to v. Incidentally, it should be clear that the terminology "inverse problem" refers to tomography, but "inverse step" refers to one of the two steps (forward or inverse steps) in solving every tomography problem.

Unfortunately, the integral equations in Equation (4) are unsolvable for a wide range of 3D EM inverse problems, especially biomedical ones. Moreover, the function G itself is only well known for those backgrounds without any boundary (like an antenna radiating in free space) or backgrounds whose boundary structures are simple. The Hankel function is an example of an analytic Green's function whenever the domain is not bounded or its boundary is simple. However, when the boundaries are complicated and some boundaries carry surface charges and currents (which happens in many EM problems), these surface charges and currents cannot be modeled as volume charges and currents, so they are integrated to give an analytic Green's function like the Hankel function. Extensive computational techniques are then required to find the Green's function (see, for example, chapter 14 of J. Jin, *The Finite Element Method in Electromagnetics*, 3rd ed., Wiley, New York, 2014 ("Jin")).

Additionally, even if G is found, another difficulty is in applying the $\nabla\nabla\cdot$ operator to the non-integrable singularities of the Green's function in the galvanic integral term, as described in Chew. Hence, the integral equations in Equations (4), which contain the 3D Green's function, are usually solved through an inefficient and time-consuming iterative process. In biomedical microwave tomography problems that require rapid solutions, the following approximations are usually made to allow Equation (4) to be solved efficiently:

(i) In cases where the 3D Green's function is not loadable due to limited available computer memory, or otherwise where the computing resources (e.g., CPU speed) are insufficient to solve Equations (4) in a reasonable time frame, the domain is approximated as being homogeneous along one axis (e.g., the z-axis), to enable 2D integration and Green's function, which are simpler and computationally feasible in practice. This approximation results in a 2D reconstructed profile of the object with the imaging antennas approximated as point sources (see FIG. 1b), while of course the imaging antennas are in reality spatially extended (as shown in FIG. 1 (a)), and the assumed homogeneity of the object along one axis is unlikely to be correct.

(ii) Even if the available memory and CPU resources are sufficient to load the Green's) function, because the galvanic integral term becomes negligible only when $\varepsilon(q)/\varepsilon_b(q) \approx 1$, a background matching medium, which has mathematically complex dielectric properties in many problems (e.g., in biomedical problems where tissues of the body are lossy), is used to provide dielectric properties that are close to the average dielectric properties of the imaged object. This approach enables the galvanic term to be neglected and avoid the problems associated with the singularities of the Green's function. In other words, the matching medium improves the match between the antenna and the outer layer of the imaged object. The benefit of using the background matching medium is to greatly reduce the computational complexity of the problem, and may be required to make the problem computationally feasible. For example, the average relative dielectric property of the human head is $\varepsilon_{ave} \approx 42-j13.1$ at 1.6 GHz. Accordingly, to image the human head at this frequency using integral-based microwave tomography, the background medium should have dielectric properties close to this complex value. Of course, manufacturing a background medium having such a specific complex value can be technically challenging, complicates the imaging system and adds more attenuation and thus reduces the system's dynamic range. Moreover, in practice the background medium does not perfectly match the antennas to the imaged object, and yet the galvanic term is entirely ignored in the calculations. Indeed, this is why the reconstructed conductivity, which is relevant to the galvanic term in integral-based (i.e., prior art) tomography, is usually less accurate than the reconstructed relative permittivity. In addition, putting objects such as human organs in the background medium may be another difficulty and cause some discomfort to the patient. It should be noted that the inductive term is not negligible when using the background matching medium because this term is multiplied by $k_b^2$ which is large at microwave frequencies.

These approximations simplify the problem domain from that shown in FIG. 1a to that shown in FIG. 1b, and yield a reduced two-dimensional form of Equation (4) as:

$$\text{forward} \left\{ E^{inc}(p') = E(p') - k_b^2 \underbrace{\int_{\Omega'} G(p' - q')\left(\frac{\varepsilon_r(q')}{\varepsilon_b(q')} - 1\right) E(q') dq'}_{inductive} \right. \tag{5}$$

$$\text{Inverse} \left\{ E_j^{sct} = k_b^2 \underbrace{\int_{\Omega'} G(p_j' - q')\left(\frac{\varepsilon_r(q')}{\varepsilon_b(q')} - 1\right) E(q') dq'}_{inductive} \right.$$

where the primed variables are the 2D versions of their unprimed 3D variables in Equation (4).

In order to solve Equation (5), linear or nonlinear optimization techniques are utilized to minimize a cost functional defined as the energy mismatch between the calculated and the measured data. Using either Born's or Van Den Berg's methods, an iterative process is utilized and a cost functional, defined as the energy mismatch between the calculated and the measured data, is minimized by optimization. The 2D forward-inverse problem iterates until the cost functional becomes stable and does not vary with additional iterations. However, as Equation (5) is an underdetermined problem where the number of unknowns is much more than the number of knowns (given data), the number of measurements must be high enough to have reasonably accurate results. Also, the stable cost functional will not be achieved as $\varepsilon(q')$ is clearly unbounded, and no additional condition is implemented to confine the possible solutions of $\varepsilon(q')$, unless a regularization is applied to confine $\varepsilon(q')$. Without regularization, the cost functional may diverge during the iteration process.

Although the accuracy of the final results can be improved by increasing the number of antennas (though to a limited certain value defined by the degree-of-freedom theory), this comes at the cost of increasing the computation time. Consequently, the number of imaging antennas represents a tradeoff between accuracy and computation time. In emergency cases such as strokes, and road or sport accidents where time plays a key role in the chance of survival or disability, the use of a portable or on-site microwave tomography system may preclude the use of a large number of antennas, but this choice may also preclude the obtaining of accurate results, and thus increase the risk of missing a significant diagnosis such as an intracranial haematoma, for example.

In order to address the shortcomings of existing methods for solving electromagnetic inverse problems, which are invariably based on integral equations, the inventors have developed a new tomographic imaging system and process that involves solving electromagnetic inverse problems using partial differential equations.

The new differential framework enables solving electromagnetic inverse problems by computational techniques such as the finite element method (FEM) which is not based on the Green's function and thus, does not face the limitations described above. This is particularly important when tomography is implemented for medical emergencies where rapid image reconstruction is critical.

Equation (1) can be used as the differential equation for the forward step. In Equation (1), the boundary conditions play a bounding role for $\vec{E}$, forcing it to take values that agree with the boundary values. Indeed, these boundary conditions play a regularizing role. To establish the differential equations and their corresponding boundary conditions for the inverse step, the third Maxwell equation expressing the divergence of the displacement (D) vector according to the volume charge density $\rho$ is utilized as:

$$\nabla \cdot D = \rho \qquad (6)$$

where either D or $\rho$ are generally functions (vector and scalar, respectively) of three-dimensional spatial coordinates. Since in many practical EM problems, e.g. biomedical ones, no volume charge exists in the domain (a similar assumption used in the integral-based equations in (4)), $\rho=0$ is assumed. Since the displacement itself is a function of the electric field and permittivity, it follows that:

$$\nabla \cdot (\varepsilon E) = 0 \qquad (7)$$

In the described embodiments, Equation (7) is used as the differential equation in the inverse step and Equation (1) is used as the forward step to solve the electromagnetic inverse problems using three-dimensional spatial coordinates. Some manipulations on Equation (7) gives:

$$(\nabla \cdot E)\varepsilon + E \cdot \nabla \varepsilon = 0 \qquad (8)$$

Equation (8) describes the permittivity, as a first-order differential scalar function, while the electric field in Equation (1) is a second-order differential vector function. As will be apparent to those skilled in the art, the partial differential equations (1) and (8) only govern their corresponding quantities within the problem domain, not at any boundary, edge, etc., where a discontinuity (non-differentiability) may take place. For those boundaries, other governing equation referred to in the art as "boundary conditions" or "boundary equations" describe the corresponding physical quantities (i.e. $\vec{E}$ and $\varepsilon$) on the boundaries and edges, are used. These boundary equations are either zero-order or first-order differential, as seen in equation (1) for $\vec{E}$. Accordingly, it is quite clear why a problem governed by partial differential equation does not have a specific solution unless its boundary conditions are determined.

To define the boundary conditions that enable solving Equation (8), the definition of permittivity can be used as an insight by which the rest of the methodology is established. The permittivity of a system of materials is the capacitance of the system per unit length in storing electric energy, the SI unit of permittivity being Farad/meter. This means that the boundary condition of permittivity on each specific boundary represents the "capacitance of the system per unit length" seen by that boundary. Like Equation (1), three types of boundary conditions are required in Equation (8) for: (i) the antenna surface, (ii) any dielectric surfaces in the problem where the average permittivity of the unknown object is given and can be used as a priori information (on the boundaries of this average object, the condition $\varepsilon_1 \vec{E}_{1n} = \varepsilon_2 \vec{E}_{2n}$ is applied where the normal components of the electric field is given; opposite the forward step in Equation (1) where the permittivity is given), and (iii) the surrounding surface S. For the first and third boundaries, one can consider which electromagnetic quantities on these boundaries can satisfy the SI unit of permittivity. Clearly, the SI unit of permittivity can be rewritten as $$\frac{\text{Ampere} \cdot \text{second}}{\text{Volt} \cdot \text{meter}}.$$

This ratio can be calculated on each boundary using the right-hand side of the second Maxwell equation where permittivity links the electric field to current density $\vec{J}$ as:

$$\vec{J} = j\omega\varepsilon\vec{E} \qquad (9a)$$

Applying the dot product of the current density to the two sides of Equation (9a) gives:

$$\vec{J} \cdot \vec{J} = j\omega\varepsilon\vec{E} \cdot \vec{J} \qquad (9b)$$

Simplifying the dot product gives the following equation for the complex permittivity:

$$\varepsilon = \frac{J_t^2 + J_n^2}{j\omega J_t E_t + j\omega J_n E_n} \qquad (9c)$$

where t and n stand for the tangential and normal components, respectively. Equation (9c) is indeed the complex permittivity (capacitance per unit length) seen by each boundary.

Equation (9c) is applied to the boundaries of interest. On the antenna conducting faces (e.g., a dipole with a small thickness, made of copper), the tangential component of the electric field i.e. $\vec{E}_t$, is almost zero. In this case, $\vec{J}$ still possesses two components: the tangential conduction component $\vec{J}_t$, which is mainly due to the tangential component of the magnetic field on the antenna's surface, and the normal displacement component $\vec{J}_n$, which is due to the normal component of the electric field $\vec{E}_n$. Therefore, the boundary equation on the antenna surface can be expressed as:

$$\varepsilon = \frac{J_t^2 + J_n^2}{j\omega J_n E_n} = \varepsilon_p + \varepsilon_0 = \varepsilon_{look} \qquad (9d)$$

where $\varepsilon_{look}$ is the complex permittivity of the domain seen by each imaging antenna. Moreover, $\varepsilon_p$ is the complex permittivity of the system, seen by each antenna due to the "perpendicularity" of the conduction current (which is tangential) with respect to the electric field (which is normal) on the antenna. As $\vec{E}_n$ supports a surface charge on the antenna conductor face, each imaging antenna possesses a specific conduction current density $\vec{J}_t$ and surface charge $\rho_s$ on its surface, indicating a specific seen capacitance. Before deriving the boundary condition for the surrounding surface S, it is noted that representing equation (9c) in another possible form might lead to an incomplete equation. For example, if the definition of the permittivity is taken as:

$$\vec{J} = j\omega\varepsilon\vec{E} \qquad (9e)$$

$$\Rightarrow \vec{J} \cdot \vec{E} = j\omega\varepsilon\vec{E} \cdot \vec{E}$$

$$\Rightarrow J_t E_t + J_n E_n = j\omega\varepsilon(E_t^2 + E_n^2)$$

$$\Rightarrow \varepsilon = \frac{J_t E_t + J_n E_n}{j\omega E_t^2 + j\omega E_n^2}$$

then, as $\vec{E}_t$ is almost zero on the antenna conducting surface, equation (9c) reduces to $$\frac{J_n + E_n}{j\omega E_n^2} = \varepsilon_0.$$

However, this equation is not complete because it does not consider the effect of $\vec{J}_t$. This incompleteness comes from the fact that the presence of $\vec{J}_t$ on the conducting surface of the antenna, as per the EM boundary conditions, is due to the tangential component of the magnetic field, not the tangential component of the electric field. Hence, zero value for $\vec{E}_t$ does not assign a zero value to $\vec{J}_t$.

The surrounding surface S, on the other hand, has no physical interface (such as a conducting antenna face) to carry the conduction current density, the current density in Equation (9c) will be only the displacement one ($\vec{J}_{displacement} = j\omega\varepsilon_0\vec{E}$) and the boundary condition Equation (9c) reduces to:

$$\varepsilon = \frac{\vec{J}_{displacement} \cdot \vec{J}_{displacement}}{j\omega\vec{E} \cdot \vec{J}_{displacement}} = \varepsilon_0 \qquad (10)$$

These boundary conditions, which are of the Dirichlet and continuity types, supplement Equation (8) to bound the possible distributions of permittivity within the domain (undertaking a regularizing role). Therefore, the complete equation for the inverse step in the proposed partial differential format reads (8) as the domain equation $$BC: \begin{cases} \varepsilon = \varepsilon_{look} & \text{(on antennas)} \\ \varepsilon_1\vec{E}_{1n} = \varepsilon_2\vec{E}_{2n} & \text{(on dielectrics)} \\ \varepsilon = \varepsilon_0 & \text{(on } S\text{)} \end{cases} \qquad (11)$$

The only remaining question is how to calculate $\varepsilon_{look}$. To this end, Appendix I provides a derivation of the normal component of the electric field and the conduction current density on the conducting antenna surfaces under the measured S-parameters utilizing, for example COMSOL Multiphysics software.

The next step is to solve Equations (1) and (11), and this can be done using the numerical technique known as the Finite Element Method ("FEM"). Detailed discussions on how to implement and use FEM to numerically solve differential equations of the general form of Equations (1) and (11) can be found in Jin, for example.

Figure 2:
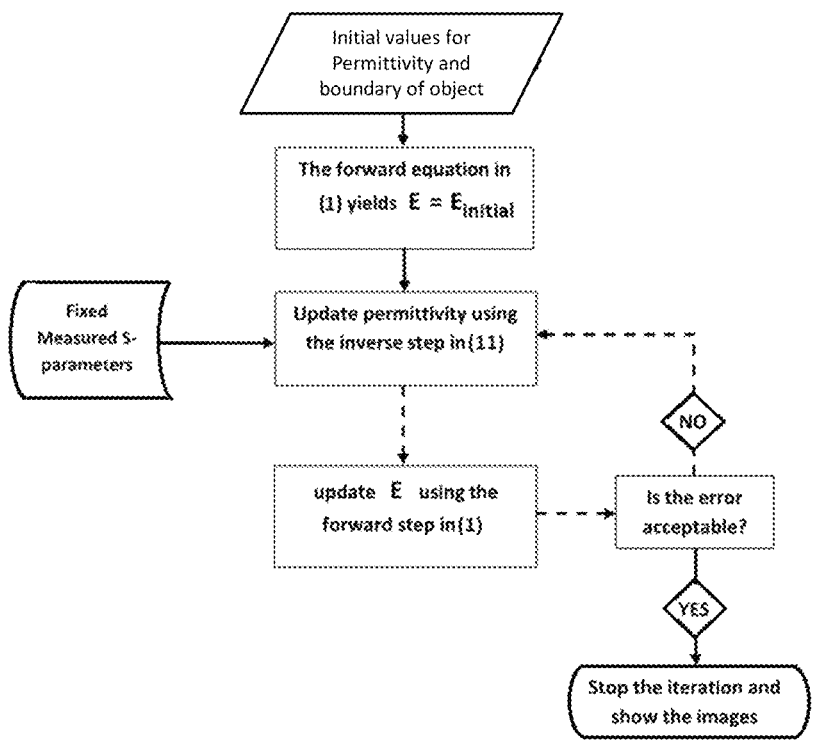
FIG. 2 is a flowchart of a tomographic imaging process that solves differential format EM inverse problems represented by Equations (1) and (11): After the first two initial steps, the fixed measured S-parameters are used to define the boundary conditions in Equation (11) and they remain unchanged during the subsequent iterations, which continue until the FEM error degree reaches a predefined (acceptable) value; the dashed loop represents the iterative loop, and (1) or (11) indicates their FEM representations.

The high level steps for solving Equations (1) and (11) are shown in the flowchart of FIG. 2 and are described below in the context of imaging a human head. At first, a boundary detection method is used to generate a contour of the three-dimensional boundaries of the imaged object (head). The average healthy dielectric properties are used as an initial guess for $\varepsilon$ in Equation (1), and then a value for E (actually three values for the three components of the electric field) is (are) derived. This E is then substituted in the FEM representation of Equation (11) to find an updated value for $\varepsilon$ (from this step on, the fixed measured S-parameters are used to define the boundary conditions in Equation (11) as described in Appendix I below; they remain unchanged during the iterations). The updated value for $\varepsilon$ is then substituted in the FEM representation of Equation (1) to give an updated value for E. After each iteration, the linear FEM optimization checks the error level in $\vec{E}$ and $\varepsilon$ with respect to their boundary conditions. This iterative process is repeated until the updated values do not change substantially with respect to their values in the previous iteration, indicating that the error reaches a small value. This process deals with two linear FEM systems of equations like $[A]_{M' \times M'}[x]_{M' \times 1} = [b]_{M' \times 1}$ in either forward or inverse step. Hence, the unknown matrix at each step is derived as $[x]_{M' \times 1} = [A]_{M' \times M'}^{-1}[b]_{M' \times 1}$, because FEM stiffness matrix $[A]_{M' \times M'}$ is invertible (M' is the total number of nodes in the problem domain).

On the robustness of the process of FIG. 2 with respect to the integral-based process of Equations (4) or (5), the space of possible solutions for $\varepsilon$ in Equations (4) or (5) is usually large because $\varepsilon$ is not subject to bounding conditions. To bound the possible solutions of $\varepsilon$, regularization techniques such as Tikhonov or "total variation" (TV) are utilized to prevent the algorithm from divergence, or convergence to a non-optimal solution (local minima). For the process described herein, however, the boundary conditions confine the possible solutions of $\varepsilon$ at the problem boundaries. Hence, utilizing another regularization scheme, like Tikhonov, is not essential, although their implementation plays a complementary role to improve the results. To solve the FEM stiffness matrix $[A]_{M' \times M'}$, techniques known by those skilled in the art such as matrix pivoting or left/right preconditioning make the problem well-conditioned and robust with respect to noisy measurements.

The solution of the inverse problem, however, is not unique for the following four reasons.

1) There is intrinsic non-uniqueness due to the presence of evanescent waves and diffraction effects.
2) The presence of local minima due to the non-linearity of most inverse scattering problems thus requiring nonlinear optimization techniques.
3) Moreover, even if a methodology such as the Born iterative method linearizes the problem as a system of equations [A][x]=[b], where [A] is the coefficient matrix, [x] is the matrix of unknowns, and [b] is the matrix of given data, [A] is not invertible (is not a square matrix) due to its under-determinacy (where the number of knowns is much less than the number of unknowns.). Hence, even if a linear optimization is utilized to solve the problem, the constructed solution may not sufficiently approach the actual one due to the under-determinacy.
4) Non-uniqueness also arises due to the sensitivity of inverse problems to noise. Indeed, even if [A] is invertible in a linear and determined problem, it is still ill-conditioned (the condition number of [A] is normally very high) so that a tiny level of noise can hugely deviate the solution of the linear system.

The first cause discussed above is unavoidable, explaining why microwave imaging is not as accurate as X-ray or MRI, but the second to fourth ones are treatable. The second, third and fourth issues in underdetermined problems can be avoided by ensuring that the number of measurements is high enough (considering the threshold of this number under the degree of freedom theory (DOF)), and regularization schemes are used to confine the space of the possible solutions. However, this is done at the expense of high computational time. On the other hand, in determined problems (as described herein), nevertheless, the second and third issues are not points of concern as well-conditioning algorithms, such as regularization techniques with sufficient number of measurements, can be used to suppress the ill-conditioned behaviour of the corresponding matrix [A]. Nevertheless, utilizing a regularization scheme for these problems solely plays a complementary role to further improve the accuracy of tomography, at the expense of increased computational time.

Whenever a problem is ill-posed, like the integral-based equations (4) or (5), the number of knowns and unknowns are not equal in the problem domain (i.e., the problem is underdetermined). Hence, regularization techniques, such as Tikhonov or "total variation" (TV), together with a sufficient number of measurements, are utilized to confine the space of possible solutions and prevent the process from converging to a non-optimal solution (local minima). For the process described herein, however, the number of knowns and unknowns are equal; i.e., the problem is "determined". Thus, the problem (the FEM stiffness matrix $[A]_{M' \times M'}$) is only ill-conditioned rather than ill-posed. To cope with this issue, matrix pivoting or left/right preconditioning is applied to the stiffness matrix of the FEM representation of both Equation (1) and Equation (11) to make the problem well-conditioned and robust with respect to noisy measurements. Hence, there are no concerns from the local minima in the process described herein.

The initialization step in the described process might appear similar to the Born method in integral-based microwave tomography. However, there are the following fundamental differences between the Born method and the described process:

(i) In Born's method $\vec{E} \approx \vec{E}^{inc}$. However, such an approximation is only used as the initial input in the differential equation framework (seen in FIG. 2). Moreover, in complicated problems where the average dielectric properties of the object are utilized to improve convergence, the above approximation is not used, even in the initial step.

(ii) No regularization (such as Tikhonov regularization) is used in the described process of the differential inverse equations, because the FEM representation of Equations (1) or (11) forms a linear and determined problem. This is quite different from the underdetermined problems in Equations (4) or (5) (see, for example, Chapters 8 and 9 of Chewto see where external regularizations are required). Additionally, as the FEM itself is a minimizer, the result of each step in FIG. 2 is an improved version of the result of the previous step. The only problem of FEM is the ill-conditioned stiffness matrix, as discussed above. Fortunately, this problem can be solved by any of several techniques known to those skilled in the art, such as pivoting and left/right preconditioning, as adopted for example in the simulator COMSOL.

In addition to the above differences in theory, unlike the integral-based equations, increasing the number of imaging antennas in the differential-based process described herein does not significantly increase the required computational time, while it improves the accuracy to some extent, keeping in mind the limitation defined by the degree of freedom theory. The relatively minor increase in the computational time of the differential-based method when using more antennas is due to the increase in the number of elements in the corresponding FEM matrix representation.

It is worth mentioning that FEM discretizes the problem domain into small elements. These elements, therefore, correspond to the resolution of the image and can be increased arbitrarily as long as sufficient computational memory is available and the computational time does not exceed the capability of the available resources. Increasing the elements, however, does not significantly improve accuracy. The accuracy can be improved by some factors discussed below. Thus, the definition of the achievable resolution in the integral-based tomography is different from the process described herein. As the integral-based methods are underdetermined, the resolution cannot be increased arbitrarily.

Since the differential-equation process described herein can be used as a localized tomography method, a multi-static radar-based beamforming process can be utilized as an auxiliary pre-scanning tool to enable the differential-based tomography to focus on the suspected volume. However, to get accurate results, radar-based imaging requires the effective dielectric properties of the imaged object from the perspective of each imaging antennas as a priori information. The beamforming process described herein uses spatial statistical techniques to model the complex permittivity of the imaging domain as a function of scattering parameters. The beamforming process does not require any predefined gap between the antennas and the imaged object, nor does it need the imaged object to be centered within the imaging domain.

Assume that an imaging domain is surrounded by $N_a$ antennas operating in a multi-static mode. The effective permittivity of the imaging domain seen by any antenna depends on the properties, size and shape of the imaged object located in the domain. For a heterogeneous object with frequency dispersive properties, the effective permittivity seen by an antenna depends also on the location of that antenna with respect to the object and the frequency used. Thus, the assumption of one effective permittivity, or even the prediction of one effective value when using radar beamforming processing techniques does not really enable accurate imaging. Thus, a process that can predict the effective permittivity seen by any antenna is important for accurate imaging.

The effective permittivity can be expressed as a function of the scattering parameters. So, if a set of S-parameters is calculated for a specific imaging domain (i.e., a specific arrangement of antennas with a specific structure) with known properties, these parameters can be used to train the process to predict the effective complex permittivity when imaging an unknown object. Such a function could be solved using a standard least squares linear regression method in a bi-static configuration. However, due to the large number of variables (S-parameters) in the described multi-static configuration, such a function leads to ill-posed problems where more than one weighting factor satisfies the linear equation, leading to over or underdetermined equations.

To address this issue, additional information is introduced to the ill-posed problem to prevent over- or under-fitting. To that end, the problem is regularized by the spatial regionalization of the scattering parameters. Thus, a variogram, which describes the degree of spatial dependence of signals, is calculated for each receiver i according to:

$$\gamma_i(h) = \frac{1}{2|N(h)|} \sum_{(j,k)\in N(h)} |S_{ij} - S_{ik}|^2 \quad (B1)$$

where h is the distance between the $j^{th}$ and $k^{th}$ transmitting antenna locations, $S_{ij}$ is the received signal at the $i^{th}$ antenna transmitted from the $j^{th}$ antenna using $N_f$ frequency samples, and N(h) denotes the set of pairs of observations ij and ik such that $|r_{ij}-r_{ik}|=h$ and $|N(h)|$ is the number of pairs in the set. Low values of h represent neighboring antennas, which receive highly correlated signals, and thus their corresponding $\gamma$ is low, whereas antennas that are distant from each other (high values of h) deliver high values of $\gamma$. By using (B1), each receiver in the multi-static configuration is presented by a function $\gamma(h)$. Therefore, $0.5 \times N_a \times (N_a+1)$ independent variables/signals are reduced to $N_a$ regularized functions that incorporate the spatial features of relevant signals.

To link $\gamma(h)$ with the dielectric properties of the imaging domain, the effective permittivity from the view point of ith receiver $\hat{\varepsilon}_i$ is modeled as:

$$\varepsilon_i(s) = f(s)w + z(s) \quad (B2)$$

where $s=\{\gamma, h\}$ is the function's input in which $\gamma$ is calculated using Equation (B1), $f(s)=[1, \gamma, h, \gamma^2, \gamma h, h\gamma, h^2]$ is a vector of quadratic regression function, and w is the 7×1 vector of regression coefficients to be calculated for a minimized error $z(s)$. There are $N_h$ functions of $\varepsilon_i$ for h values extending from 0 to the length of the maximum axis of the antenna array. Those quadratic functions relate discrete values of $\gamma$ to h and to $\varepsilon$. To obtain the best unbiased estimation of w, it is necessary to train the model using training samples, which are generated using the calculated S-parameters of the imaging domain when filled with uniform media that have certain assumed permittivity values (sample media). In that regard, the imaging domain is assumed to have $N_\varepsilon$ different permittivity values $\varepsilon_{n\,(n=1\,to\,N_\varepsilon)}$, and the corresponding multistatic S-parameters are calculated at each assumption. The calculated S-parameters are then used in Equation (B1) to obtain $\gamma(h)$ and thus the corresponding training functions $s_n=\{\gamma_n, h_n\}_{(n=1\,to\,N\varepsilon)}$ and $f(s_n)$.

Assuming $N_\varepsilon$ different training samples with assumed permittivity values $\varepsilon_{n\,(n=1\,to\,N\varepsilon)}$, Equation (B2) can be written in a matrix form as $$\varepsilon_i = Fw + z \quad (B3)$$

where $\varepsilon_i=[\varepsilon_1, \ldots, \varepsilon_M]^T$ is the vector of permittivity with the dimension of M $(=N_\varepsilon \times N_h) \times 1$, $F=[f(s_1), \ldots, f(s_M)]^T$ is the M×(N−1) regression function matrix and $z=[z(s_1), \ldots, z(s_M)]^T$ is the M×1 error vector. The matrix of coefficients estimator $\hat{w}$ (the notation ^ represents the estimated coefficient) can be determined subject to the minimization of the total sum of squares (TSS) of the error, z $$TSS = \sum_{n=1}^{m} |z(s_n)|^2 = (\varepsilon - Fw)^T(\varepsilon - Fw) \quad (B4)$$

The generalized least squares solution of w is then $$\hat{w} = (F^T C^{-1} F)^{-1} F^T C^{-1} \varepsilon \quad (B5)$$

In this equation, $C=[c_{ij}]$ is an M×M stochastic-process correlation matrix with $c_{ij}=\rho(s_i, s_j)$, $i,j=1, \ldots, M$, where $\rho$ is the correlation function between the permittivity values at samples $s_i=\{\gamma_i, h_i\}$, $s_j=\{\gamma_j, h_j\}$. After testing different correlation functions, such as linear, Gaussian and exponential functions, the latter is selected as it gives the best fit to the data.

After finding $\hat{w}$ for the designed imaging domain (antenna array and its structure), the training step finishes and the system is ready to be used to image an unknown object of any shape and size, as long as it fits within that domain. In this case, the permittivity value $\hat{\varepsilon}_i$ for the measured S-parameters in the presence of an unknown imaged object with $s=\{\gamma, h\}$ is approximated by:

$$\hat{\varepsilon}_i(s) = f(s)\hat{w} + c(s)^T C^{-1}(\varepsilon - F\hat{w}) \quad (B5)$$

where c(s) is the correlation matrix between the input s from the unknown object and the training samples. Finally, the observed effective permittivity by the $i^{th}$ antenna is calculated by averaging the permittivity values over all values of h:

$$\hat{\varepsilon}_i^{effective} = \frac{1}{|N_h|} \sum_{j=1}^{N_h} \hat{\varepsilon}(s_j) \quad (B7)$$

In summary, the adopted multi-static beamforming process can be represented by the following steps:
a) Training:
1. Calculate the multi-static frequency domain S-parameters for different (training) media,
2. Regularize the S-parameters using equation (B1), and
3. Determine the vector of the coefficients estimator $\hat{w}$, using equation (B5), b) Imaging:
1. Insert the object to be imaged in the imaging domain and collect the multi-static frequency domain S-parameters with the unknown imaged object,
2. Regularize the measured S-parameters using equation (B1),
3. Estimate the effective complex permittivity vector using equations (B6) and (B7), and
4. Construct an image using the estimated permittivity values and proper imaging algorithm, such as back-projection method.
5. The generated image will show any abnormality within the object. Such an image can be adopted as an initial image for the differential tomography, which is used in this case as a local area tomography focusing on finding the dielectric properties of the suspected volume.

Unlike the integral-based methods of the prior art, increasing the number of the antennas in the differential-based method described herein does not significantly increase the computational time, while it improves accuracy, of course to a limit defined by the degree of freedom theory. In the process described herein, the relatively minor increase in computational time by using more antennas is due to the increase in the number of elements in the corresponding FEM representation. Since FEM discretizes the problem domain into small elements, these elements correspond to the "resolution" of the image and can be increased arbitrarily as long as sufficient computational memory is available and the computational time remains acceptable for emergency scenarios.

Using a coupling medium is not required for the process described herein. However, a coupling medium can optionally be used to improve the images, or if the imaging is being done in a noisy environment. To that end, a high-dielectric lossless coupling medium can be inserted in the space separating the imaging antennas from the imaged head. On the other hand, a high-dielectric medium that is extremely lossy can be inserted between and behind the imaging antennas. The first (lossless) medium operates like an EM waveguide and thus enhances the signal penetration inside the head for higher fields inside the brain, whereas the second (lossy) medium absorbs any surface waves, significantly reducing the antenna's mutual coupling and undesired reflections and thus enhances the signal to noise ratio for better imaging even in a noisy environment. Such a coupling combination has not been used in prior art tomography because the latter requires homogenous matching medium for the required Greens function for such a scenario. Moreover, to satisfy the requirements of boundary conditions when solving the problem, the outer boundary of the imaging system includes an absorbing material covered by a metallic shield.

The process described herein requires a priori information about the boundaries of the imaged object. To provide that information, the changes in the properties of the imaging antennas in the presence of the imaged object are utilized. When an antenna faces an imaging object, its reflection coefficient changes significantly due to the change in its load impedance. This change is usually seen as a frequency shift in the minimum value of the reflection coefficient (see FIG. 3) due to the frequency-dependent behaviour of the input impedance. This phenomenon is more apparent at high frequencies where a high proportion of the transmitted signal is reflected back from the skin or boundary of the imaged object. On the other hand, different distances between the antenna and the imaged object result in different load impedances and hence different antenna input impedances and shifts in the spectra of reflection coefficients. Therefore, knowing the relation between the distance of the imaged object from the antenna and its input impedance or the frequency shift of the reflection coefficient can lead to the identification of the imaged object's surface. To that end, the four different methods described below are utilized for accurate boundary detection.

Figure 3:
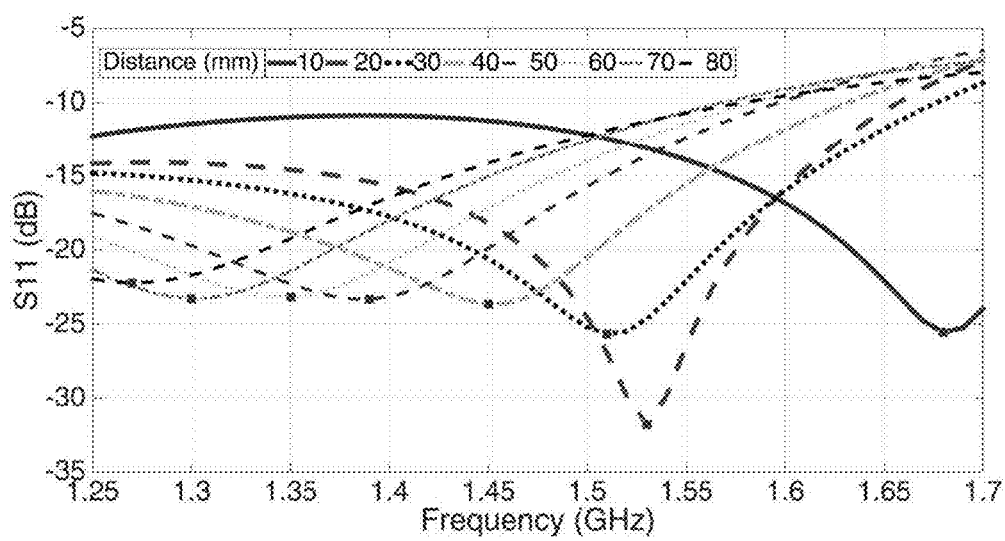
FIG. 3 is a graph of reflection coefficients of the imaging antenna as a function of frequency when facing the imaged object and for separation distances from 5 mm to 80 mm.
Figure 4:
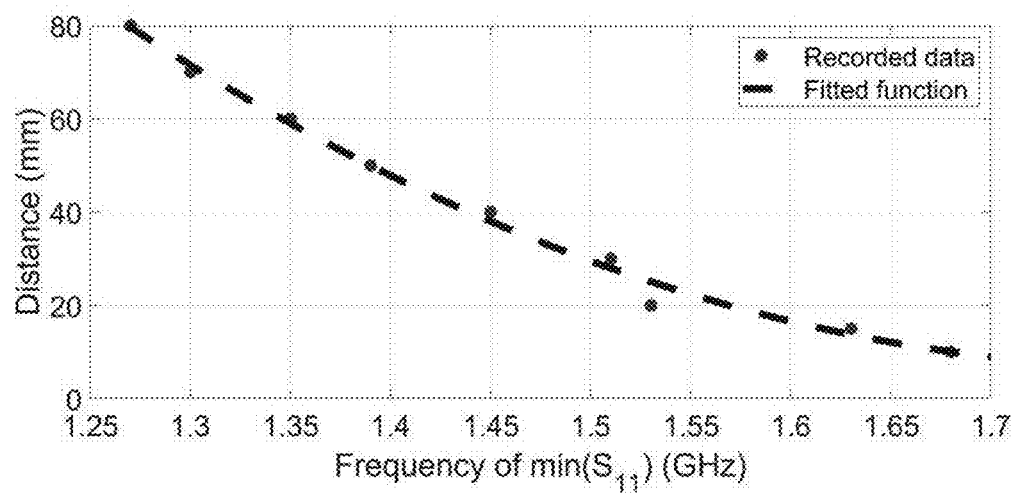
FIG. 4 is a graph of the distance between the antenna and the imaged object boundary (skin) as a function of the frequency at which the corresponding reflection coefficient is a minimum.

Method #1:

To find the relation between the resonant frequency of an antenna and the location of the imaged object, the reflection coefficients of that antenna when faced with the imaged object at different distances are determined and used to define a function representing the relationship between the distance and the frequency shift. To that end, a simulation setup in which the imaging antenna faces a numerical model representing the imaged object with its realistic dielectric properties is established. In a data acquisition step, a signal covering the used frequency band is transmitted by the antenna and the intensities of the corresponding signals backscattered from the model are recorded for different distances between the model and the antenna. For each separation distance, the backscattered signal intensity has a minimum at a corresponding frequency, as shown in FIG. 3. The resulting values are provided as inputs to a standard fitting procedure in order to determine a function representing relationship between separation distance and frequency, as shown in FIG. 4.

In the described embodiment, the resulting function is a second-order quadratic equation, as follows:

$$d=af_m^2+bf_m+c \quad (12)$$

where d is the distance between the antenna and the skin, $f_m$ is the frequency (in GHz) at which the reflection coefficient is minimised, and a, b, and c are fitting parameters dependent upon the antenna. Knowing the location of the imaging antennas, the imaged object's surface can be estimated by using the obtained equation for all of the antenna array elements arranged around the object. In this manner, a set of points with number equal to the number of antennas is generated. Connecting all of those points in the imaging domain creates an estimated surface of the object.

However, due to the limited number of imaging antennas, the estimated surface points may not cover the entire boundary of the object. To address this difficulty, the backscattered signal intensities from the actual antenna array are used to estimate the backscattered signal intensities that would be obtained from a virtual array having a larger number of antenna elements than the real array. The virtual array method uses spatial interpolation techniques to predict the received signals at the location of the virtual-elements, using the recorded signals S and antenna locations r of the real antennas according to:

$$\hat{S}(r_v)=r(r_v)\hat{w}+c(r_v)^TC^{-1}(S-R\hat{w}) \quad (13)$$

where $\hat{s}(r_v)$ is the estimated signal at virtual location $$r_{v,R}=[r(r_1),r(r_2),...,r(r_{N_\sigma^2})]^T$$

is a function matrix of the antenna locations, $\hat{w}$ is the coefficients estimator:

$$\hat{w}=(R^TC^{-1}R)^{-1}R^TC^{-1}S \quad (14)$$

and $C=[\rho(r_i,r_j)]$ is an exponential correlation matrix with:

$$\rho(\vec{r}_i,\vec{r}_j)=\frac{\langle\vec{E}(\vec{r}_i)\cdot\vec{E}^*(\vec{r}_j)\rangle}{\langle|\vec{E}|^2\rangle}=\frac{1}{4\pi^2}\int_{\phi_j}\int_{\phi_i}e^{-i\vec{k}|r_i-r_j|}d\phi_id\phi_j=e^{-i\vec{k}|r_i-r_j|} \quad (15)$$

The minima of the predicted signals at virtual locations of the virtual array are determined and their frequencies are applied to Equation (12) to determine the distance between the antennas (including real and virtual ones) and the location of the imaged object.

Method #2:

The calibration method used in vector network analyser (VNA) one-port calibration (see *Network Analyzer Basics*, Keysight Technologies 2014, available at http://literature.cdn.keysight.com/litweb/pdf/5965-7917E.pdf) can be used to relate the measured the measured $S_{11}$ of an imaging antenna to the distance of the imaged object from that antenna.

Assuming that the imaged object is located at a distance d from the antenna and has a reflection coefficient $\Gamma_d$, which can be calculated using the effective permittivity of the object, it can be easily proved from the VNA one-port calibration that the following relation is applicable to the case of an antenna radiating in proximity to a dielectric object, such as the head:

$$\frac{d_o}{d}\Gamma_d e^{-2jkd} = \frac{S_{11} - S_{11o}}{E_1 + (S_{11} - S_{11o})E_2} \quad (16)$$

where $S_{11o}$=Measured $S_{11}$ without the imaged object;

$d_o$=Minimum distance for this relation to be applicable (a factor that depends on the antenna design);

$E_1$=Error as the reflector does not reflect the whole radiated signal but only part of it (due to $S_{21}$ and should be less than 1);

$E_2$=Error as not all the reflected signal is picked by the antennas (due to $S_{22}$); and k=free-space propagation constant (=$2\pi/\lambda_o$).

So to make an accurate prediction of the distance, the system is calibrated via full-wave simulations or measurements with and without a realistic model of the imaged object at different positions from the antenna to get $S_{11o}$, $d_o$, $E_1$, $E_2$. Equation (16) is then used with the measured $S_{11}$ to find the distance d. Since the real and imaginary parts of Equation (16) can be used to calculate d at each used frequency, any of the optimization methods, such as the least square error method, can be utilised to get the most accurate prediction.

Method #3:

Image theory, as described in *Antenna theory, analysis and design*, Balanis, 2005 ("Balanis"), is a well-known method to calculate antenna mutual coupling, and can be used to include the effect of the imaged object on the input impedance of the antenna. To that end, the effect of the object can be replicated by adding a virtual antenna located at a distance 2d from the original antenna. From mutual coupling theory, it is possible to define the input impedance of the antenna as the combination of self-impedance and mutual coupling impedance:

$$Z_i = Z_s + Z_m = (R_s + R_m) + j(X_s + X_m) \quad (17)$$

Using the induced EMF method described in Balanis, it is possible to calculate the mutual impedance. As an example for antennas operating in the dipole mode, it is possible to show that mutual impedance can be approximated as:

$$R_m = R_0[2C_i(2dk) - C_i(k(2d+l_o)) - C_i(k(2d-l_o))] \quad (18)$$

$$X_m = X_0[2S_i(2dk) - S_i(k(2d+l_o)) - S_i(k(2d-l_o))] \quad (19)$$

Where $C_i$ and $S_i$ are the cosine and sine integral, respectively, and $R_0$, $X_0$, and $l_0$ are constants to be found, and depend on the configuration of the antenna. For simple dipole antennas, the parameters $R_0$, $X_0$, and $l_0$ can be found as 30, 30 and the length of the dipole, respectively. However, for complicated antennas, those parameters have to be found based on the antenna's configuration or simply by training the equation in full-wave simulations or measurements. The self-impedance depends on the structure of the antenna and can thus be calculated from the final design of the antenna using any of the methods, such as Integral Equation-Moment or Induced EMF methods.

The resonance frequency of the antenna can be calculated as the frequency at which the imaginary part of the effective input impedance of the antenna becomes zero:

$$X_s + X_m = 0 \quad (20)$$

Thus, by observing the resonant frequency of the antenna and using Equations (19) and (20), the distance between the head and the antenna can be calculated.

Method #4

The measurements across the utilized band without the imaged object and then with that object can be used to estimate the boundary of the object. Frequency domain reflection coefficients are measured at various points around the object. Each of these measurement points is converted to a spatial domain measurement by using a frequency to time domain transform. This can be done via a Fourier transform if a uniform distribution of frequency points is used, or a sum of complex exponentials otherwise:

$$s_n(t) = \sum_m \Gamma_n(f_m) \exp\left(\frac{j4\pi f_m}{c}t\right) \quad (21)$$

where $s_n(t)$ is the time domain equivalent signal.

These time domain signals are mapped to a physical space by taking into account the geometry of the antennas. The first reflection at each antenna signifies the boundary of the body under test. To enhance the boundary edge in different ways, different operations can be performed before estimation, which include taking the magnitude (absolute value or square of the absolute value) of $s_n(t)$.

An additional stage of processing can also be performed afterwards, which involves first dividing the physical space into voxels of an appropriate dimension. The contribution of each antenna to that voxel is summed by finding the propagation distance through free space. Unlike the imaging step, the dielectric properties and associated changes in propagation speed are not considered, as only the first reflection which is the boundary between free space and the body under test is considered.

Having determined the object boundaries by one of the above methods (or by any other method), and the initial 3D head image including the rough location of the suspected volume using the multi-static beamforming process described above, Equations (1) and (11) are solved. In practice, different computational methods can be used to solve the differential equations of Equations (1) and (11), but the most common of these methods are finite difference and finite element methods, which are standard methods well known to those skilled in the art, and may be provided, for example, by existing software packages (as they are in the Examples described below).

Figure 5:
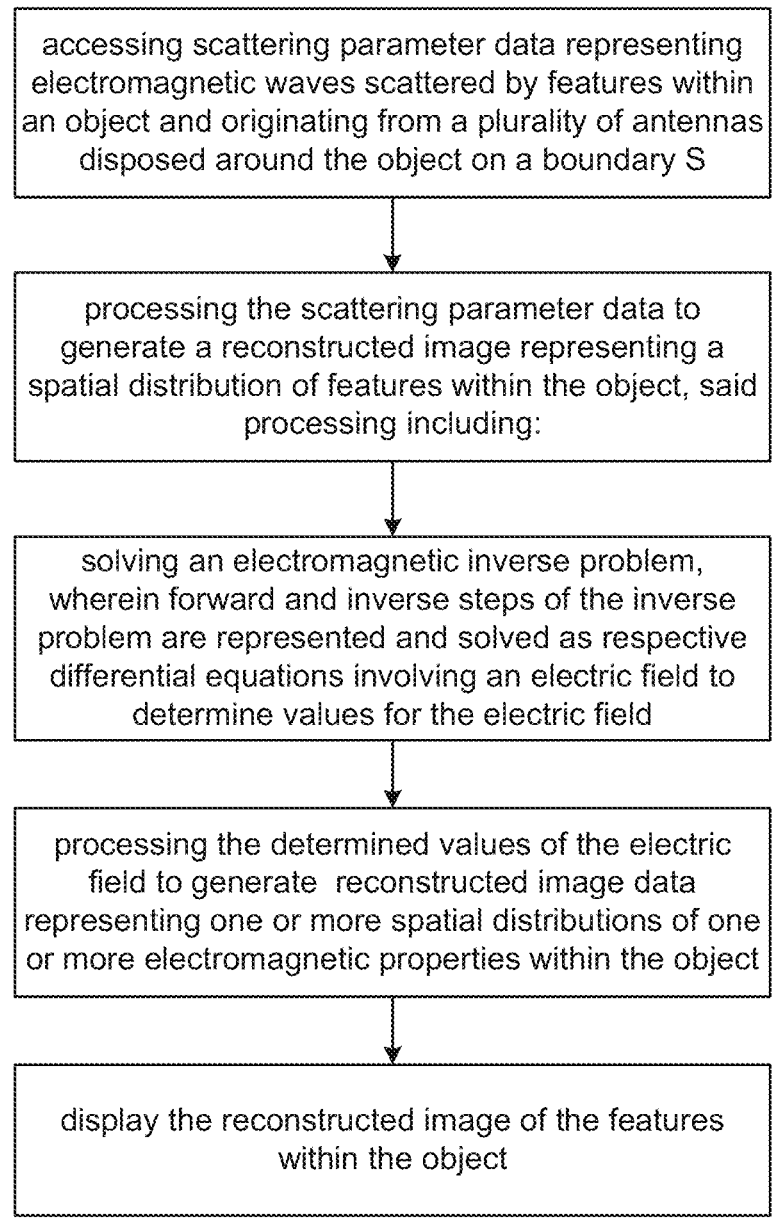
FIG. 5 is a flow diagram of a tomographic imaging process in accordance with some embodiments of the present invention.
Figure 6:
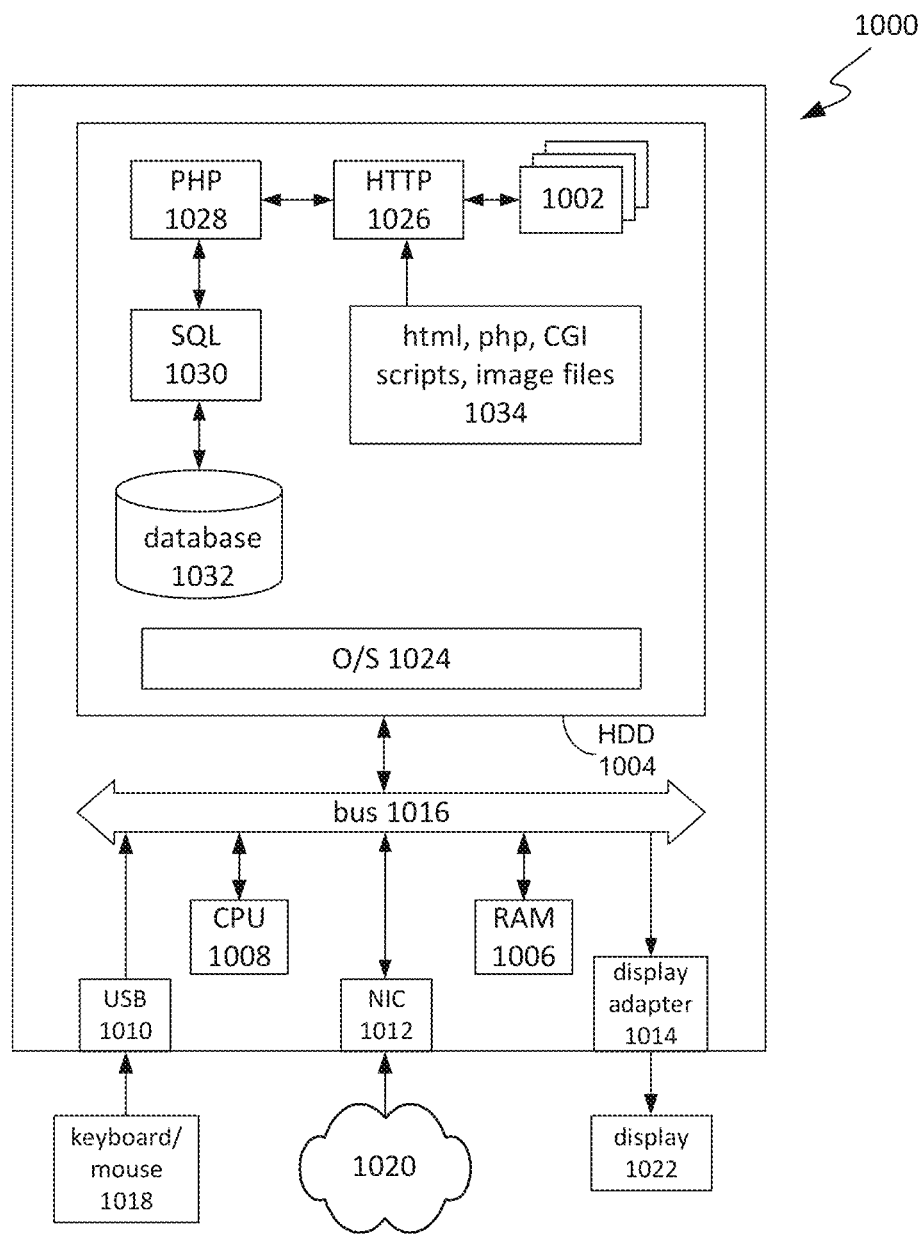
FIG. 6 is a block diagram of a tomographic imaging system in accordance with some embodiments of the present invention.
Figure 10:
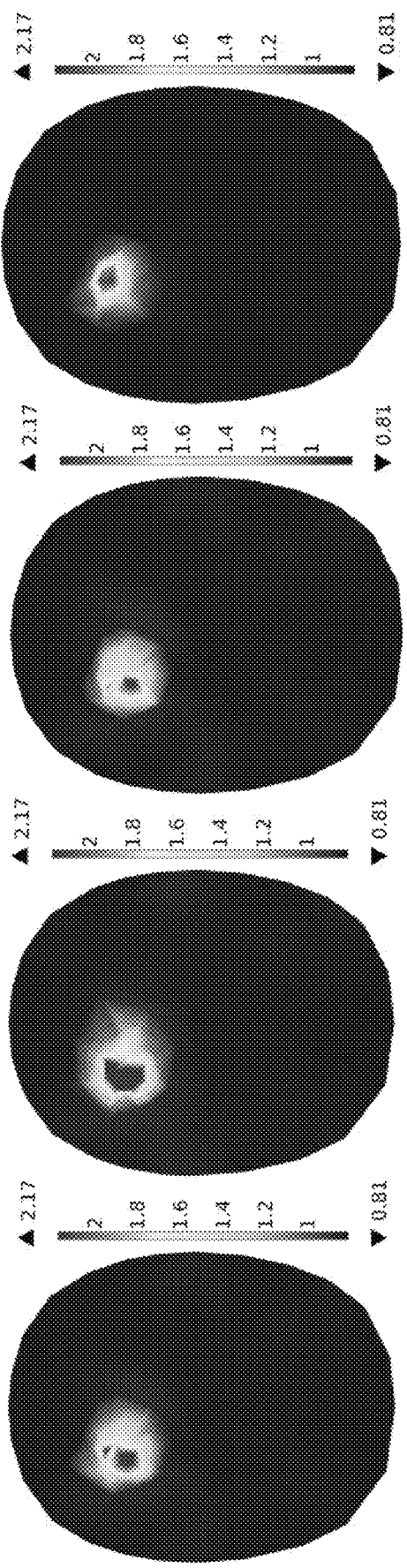
FIG. 10 corresponds to the images of FIG. 9, but showing the two-dimensional spatial distribution of conductivity σ rather than relative permittivity.

In the described embodiments, as shown in FIG. 6, the tomographic imaging system 900 includes an Intel Architecture data processing system, and executes a tomographic imaging process as shown in FIGS. 2 and 5 and described herein, the process being implemented in the form of programming instructions of one or more software modules 1002 stored on non-volatile (e.g., hard disk or solid-state drive) storage 1004 associated with the computer system, as shown in FIG. 10, and configured to solve the differential equations (1) and (11). In the described embodiments, the software modules 1002 implementing the tomographic imaging process include the commercially available computational software package COMSOL Multiphysics. However, it will be apparent that the tomographic imaging process could alternatively be implemented in the form of one or more dedicated hardware components, such as application-specific integrated circuits (ASICs) and/or as configuration data of at least one field programmable gate array (FPGA), for example.

In the embodiment of FIG. 10, the system 1000 includes a random access memory (RAM) 1006, at least one processor 1008, and external interfaces 1010, 1012, 1014, all interconnected by a bus 1016. The external interfaces may include universal serial bus (USB) interfaces 1010, at least one of which is connected to a keyboard 1018 and a pointing device such as a mouse 1019, a network interface connector (NIC) 1012 which connects the system 1000 to a communications network such as the Internet 1020, and a display adapter 1014, which is connected to a display device such as an LCD panel display 122. The system 1000 may also include one or more standard software modules 10 to 1030, including an operating system 1024 such as Linux or Microsoft Windows, and optionally web server software 1026 such as Apache, available at http://www.apache.org.

The tomographic imaging process and system described herein enable the generation of a 3D reconstructed image of features within an object (e.g., a human head) in a fraction of the time taken by prior art tomographic imaging systems and processes to generate results to the same accuracy and using the same computational hardware.

In particular, 2D reconstructions that take hours using existing state of the art methods can be three-dimensionally generated in seconds by the tomographic imaging system and process described herein.

EXAMPLES

The efficiency of the differential format of the EM inverse problems was verified by solving some 3D problems. All the simulations were done using a personal computer having an Intel Core™ i7 processor at 3.60 GHz and 16 GB of RAM. The software used for imaging was COMSOL Multiphysics, which is based on the finite element method, including the COMSOL RF Module, which is based on Equation (1). As known by those skilled in the art, this software provides an interface called Mathematics Module, which enables the user to utilize any type of partial differential equation. Accordingly, these two COMSOL modules were used to reconstruct the images, with the RF Module solving Equation (1) as the forward step, and the Mathematics Module solving Equation (11) as the inverse step. It is noted that when using the COMSOL modules, the setup of the problem must include both (1) and (11) within one "study" framework. If they are separately solved in two frameworks, their convergences will be independent, and the iterative process of FIG. 2 is not realized.

In all of the examples described below, the imaging antenna array consists of eight half-wavelength dipole antennas with a port impedance of 75Ω. The array is circular with a radius of 13 cm, which is suitable to enclose an adult head. Moreover, the imaging frequency was 1.6 GHz, which requires a dipole length of 10 cm; this frequency provides a reasonable penetration into the human head. The outer boundary of the head was given as a priori information. No matching medium is assumed in the simulations when using the new process described herein. However, a suitable matching background was assumed when solving the problem by integral-based methods supplemented by CSI for making a comparison. The signal to noise ratio (SNR) is 20 dB in all the simulations (by adding random additive noise to S-parameters) to study the robustness of the technique in a noisy environment.

As discussed above, the new differential-based and the prior art integral-based inverse scattering frameworks have fundamental differences. When using a personal computer with limited CPU speed and memory (as is the case here), the prior art methods require dealing with Equations (5) as 2D integral-based equations, requiring an assumption of homogeneity along one axis (say z) and requiring the antennas to be considered as point sources.

Example I—Homogeneous Human Head

Figure 7:
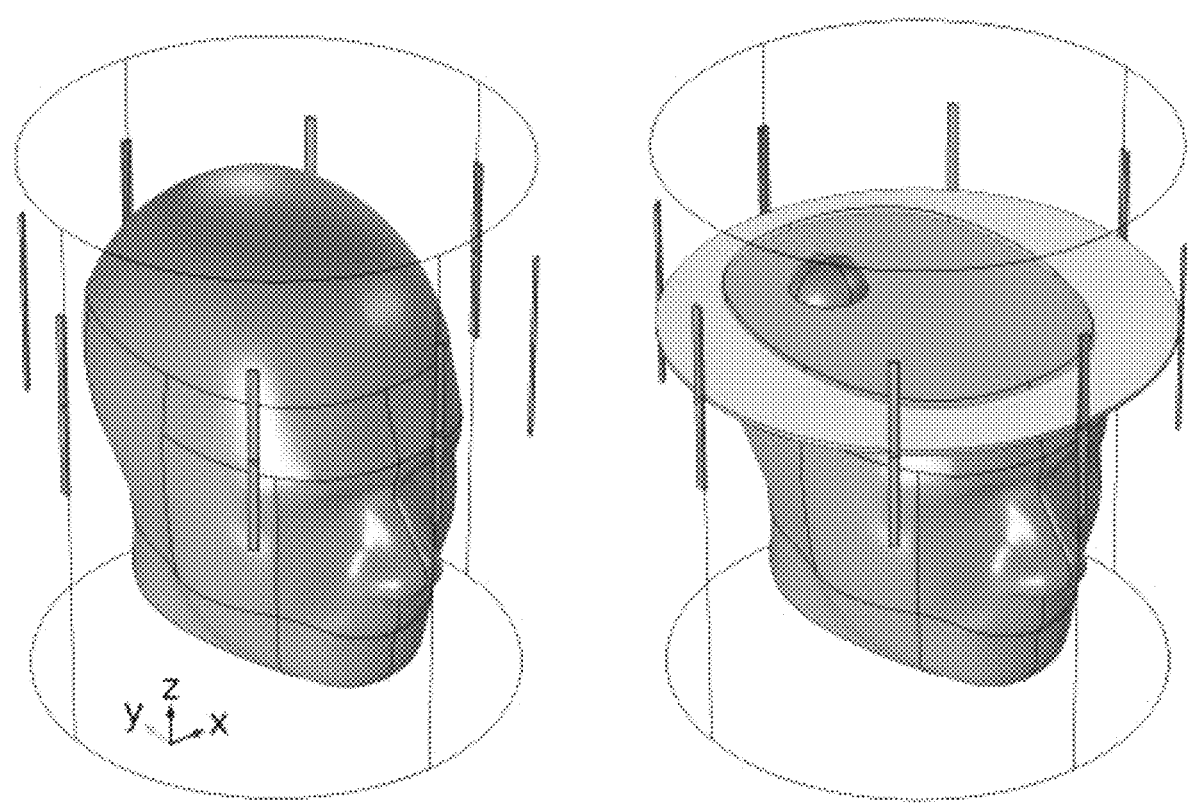
FIG. 7 includes schematic illustrations of a homogeneous human head model containing a spherical bleeding region of the brain, being imaged by the dipole antenna array; slices of the dielectric properties reconstructed by the differential process at z=15 are shown in FIGS. 9 and 10.

In the first example, a homogeneous human head (available in COMSOL) with average dielectric properties $\varepsilon_r=42$ and $\sigma=1.17$ at 1.6 GHz is imaged. To emulate a hemorrhagic stroke, a bleeding region with dielectric properties $\varepsilon_r=58.7$ and $\sigma=1.92$ at 1.6 GHz was inserted inside the brain tissue as seen in FIG. 7. This problem was solved by both the differential process described herein and by integral-based tomography supplemented by CSI method. Since CSI optimization is performed on a 2D problem described by Equation (5), it is applied to the slice z=15 cm, crossing the center of the bleeding region.

The initial value of $\varepsilon_r=1$ and $\sigma=0$ was assumed for the entire domain in the differential process. For the integral-based method, a background matching medium was used with $\varepsilon_r=40$ and $\sigma=1$, which is close to the average dielectric properties of the head at 1.6 GHz assuming the properties of the imaged object are not exactly known. The exact average value is not utilized as it will reduce the integral-based problem to a single-layer imaging problem. Indeed, the matching medium $\varepsilon_r=40$ and $\sigma=1$ was utilized to make the scenario more realistic. The FEM mesh setting for this example utilizing the differential-equation method in COMSOL Multiphysics is: Number of vertex elements: 31, number of edge elements: 257, number of boundary elements: 1449, number of domain elements: 19306.

Figure 8:
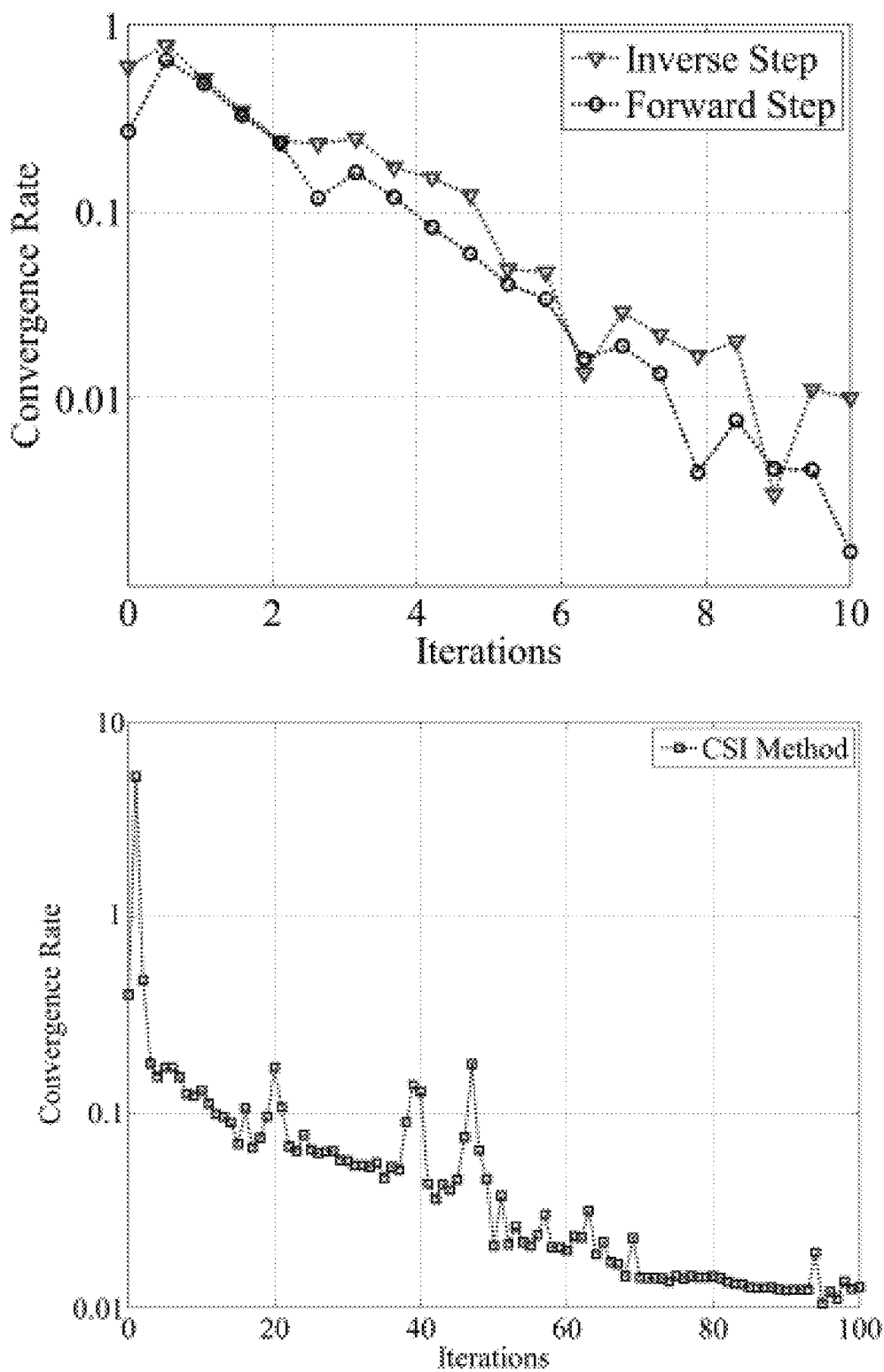
FIG. 8 includes graphs illustrating the convergence of: (a) the differential process described herein (upper graph, with forward and inverse steps shown separately), and (b) the CSI method (lower graph) for the head model of FIG. 7.

The convergence rates using the differential process and the CSI method are shown in FIG. 8 where the termination condition is set to $10^{-2}$. The number of iterations needed to get a solution was 10 and 100 in the differential and CSI methods, respectively. The element discretization in the differential process is quadratic, allowing the solver to follow the abrupt changes in a better way than the linear discretization, albeit on a longer time. Clearly, cubic discretization with highest accuracy in FEM can also be utilized, but it highly increases the computational time. Since the linear error-reduction scheme (optimization) of the differential process deals with two linear and determined systems of equations in the forward and inverse steps, each step has its own convergence rate seen in the upper graph of FIG. 8. In comparison, CSI considers both the permittivity and electric field as a single quantity (called contrast source) and thus its convergence rate contains only one plot (lower graph of FIG. 8).

The iteration time for each step in the differential process was 6 seconds for the forward step, and 5 seconds for the inverse step. Since the inverse step deals with a first-order PDE, its computational time per iteration is usually faster. In total, 11 seconds times 10 iterations will give 110 seconds reconstruction time. The iteration time for each step in the CSI method, however, is 5.8 seconds whose multiplication by 100 iterations gives 580 seconds as the image reconstruction time.

Figure 9:
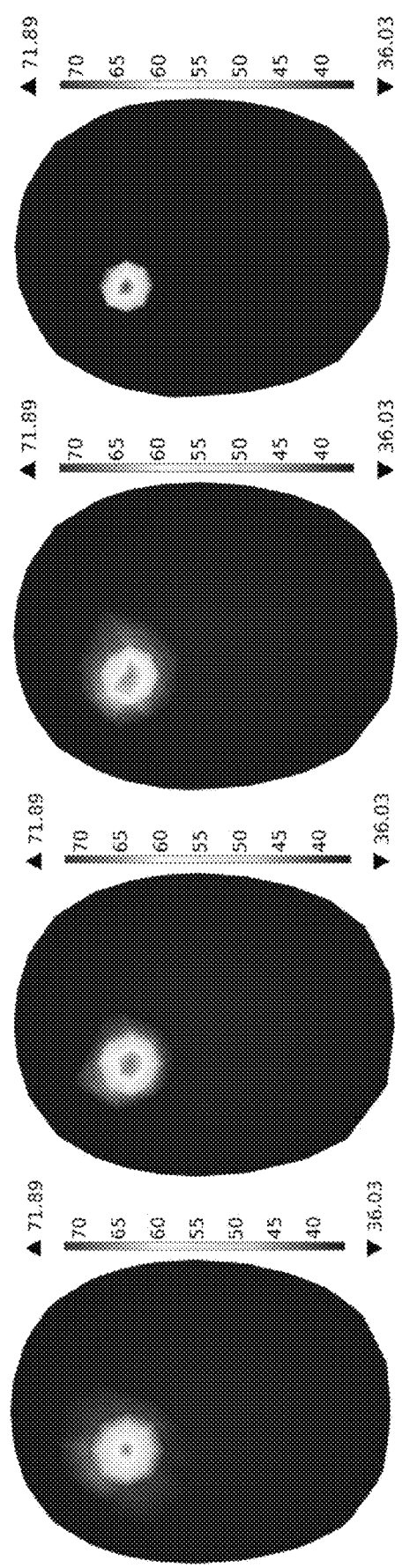
FIG. 9 includes four reconstructed images showing the two-dimensional spatial distribution of relative permittivity $\varepsilon_r$ in plan view slices through the head model: the three leftmost images were generated by the differential process for slices at z=14, 16, and 15 cm, respectively, whereas the rightmost image was generated by the CSI method for a slice at z=15 cm.

The solution of integral-based method by CSI converges slower than the differential-based process due to having fewer knowns than unknowns. FIGS. 9 and 10 show that both methods converge to a reasonably accurate result, but with an important difference; the differential process is 3D and its corresponding computational time and convergence plots belong to a large-size problem with respect to the integral-based problem (5). It is noted that the number of elements in the differential process at the compared slice (z=15 cm) is 900, which is equal to the number of pixels in CSI method to make the comparison as fair as possible. Three typical slices at z=14 cm, z=15 cm, and z=16 cm, are shown in FIG. 3 from the reconstructed 3D image of the differential process. As mentioned above, the images can be further improved by utilizing denser meshes, higher order discretizations (cubic), or increasing the number of antennas up to a specific level. The next example provides a detailed quantitative analysis of a more realistic problem.

Example II—Heterogeneous Human Head

Figure 11:
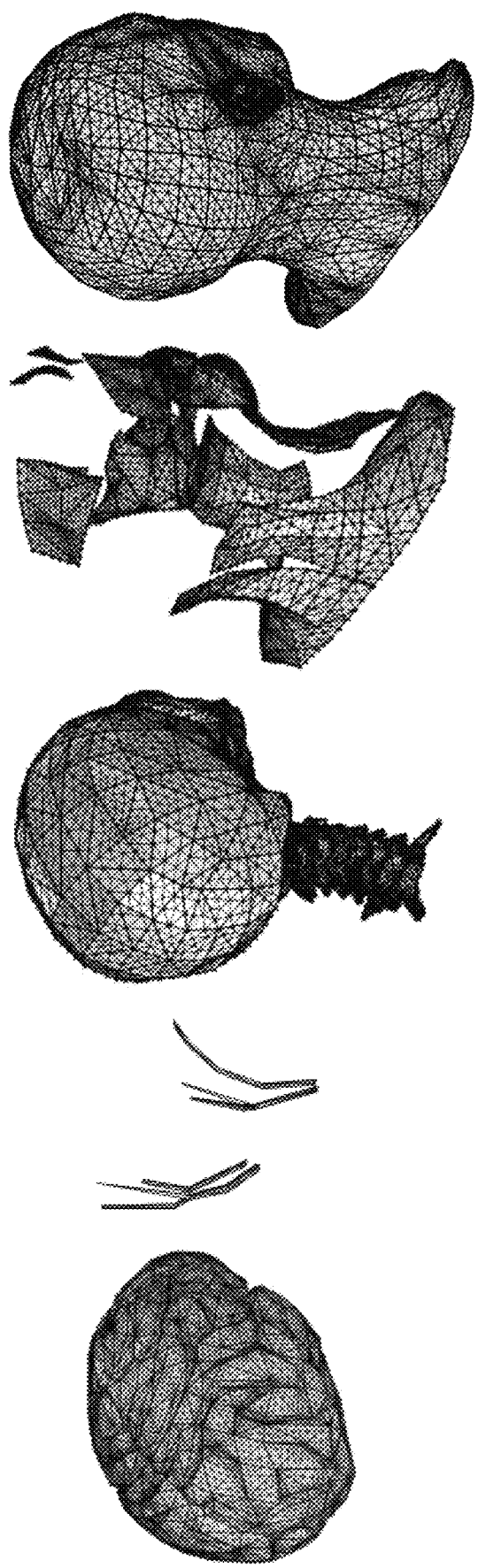
FIG. 11 includes five illustrations of different head tissues and their corresponding dielectric properties at 1.6 GHz for imaging: a) brain ($\varepsilon_r$=44, σ=1.05), b) blood ($\varepsilon_r$=58.7, σ=1.92), c) average of cortical and cancellous skull ($\varepsilon_r$=15.5, σ=0.52), d) muscles ($\varepsilon_r$=53, σ=1.25), and e) skin ($\varepsilon_r$=38.3, σ=1.1)
Figure 12:
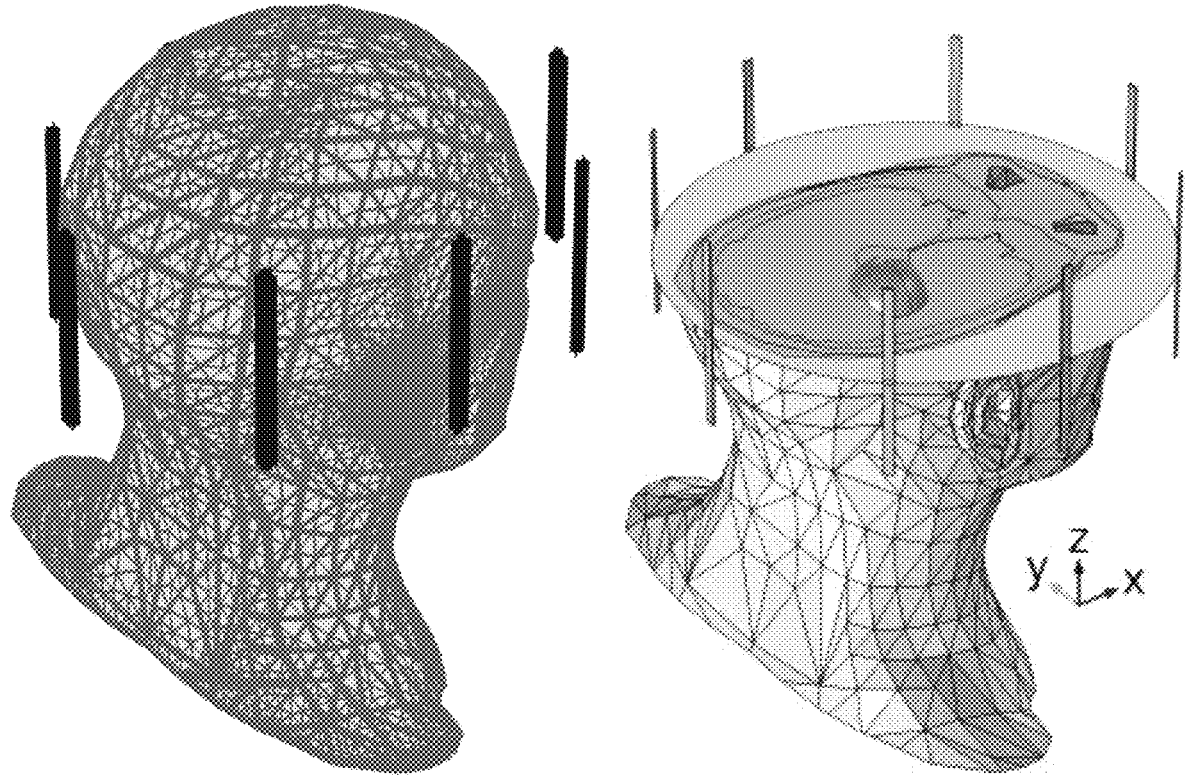
FIG. 12 includes (a) an illustration of the assembled tissues of FIG. 11, together with the imaging antennas; a slice of the 3D reconstructed relative permittivity (SI unit is 1) and conductivity (Siemens/meter) are shown in (b)

The second example considers a heterogeneous human head derived from ANSYS HFSS bio-models, with corresponding dielectric properties at 1.6 GHz as shown in FIG. 11 (a) to (e) of (a) brain ($\varepsilon_r$=44, $\sigma$=1.05), (b) blood ($\varepsilon_r$=58.7, $\sigma$=1.92), (c) average of cortical and cancellous skull ($\varepsilon_r$=15.5, $\sigma$=0.52), (d) muscles ($\varepsilon_r$=53, $\sigma$=1.25), and (e) skin ($\varepsilon_r$=38.3, $\sigma$=1.1). To emulate a haemorrhagic stroke, a bleeding region with the dielectric properties at 1.6 GHz is inserted inside the brain tissue as seen in FIG. 12, cut at the central location of the stroke z=15 cm. Among the tissues included in the simulation, the dielectric property of the brain is the average of the gray and white matters. The artery carrying blood towards the brain is considered to include the highly scattering effect of blood. The skull, which covers the brain, consists of the cortical and cancellous tissues where the average dielectric properties of these two are considered as the dielectric properties of the skull. Muscles are other important tissues included in the model, covering the skull and partly reflecting the illuminating waves due to having high dielectric properties. Finally, these muscles are covered by skin; the first layer which partially reflects the EM waves transmitted by the imaging antennas. In the initial step of the process of FIG. 2, the head is homogeneously filled by the average dielectric properties of all the tissues i.e. $\varepsilon_r$=42 and $\sigma$=1.17 at 1.6 GHz (while the rest of the domain is free space). When using (5) under CSI optimization, however, a background matching medium ($\varepsilon_r$=42 and $\sigma$=1.17) fills the entire imaging domain, including the head. Since this problem represents a multilayer heterogeneous object, the matching medium has the average properties of all included tissues.

Figure 13:
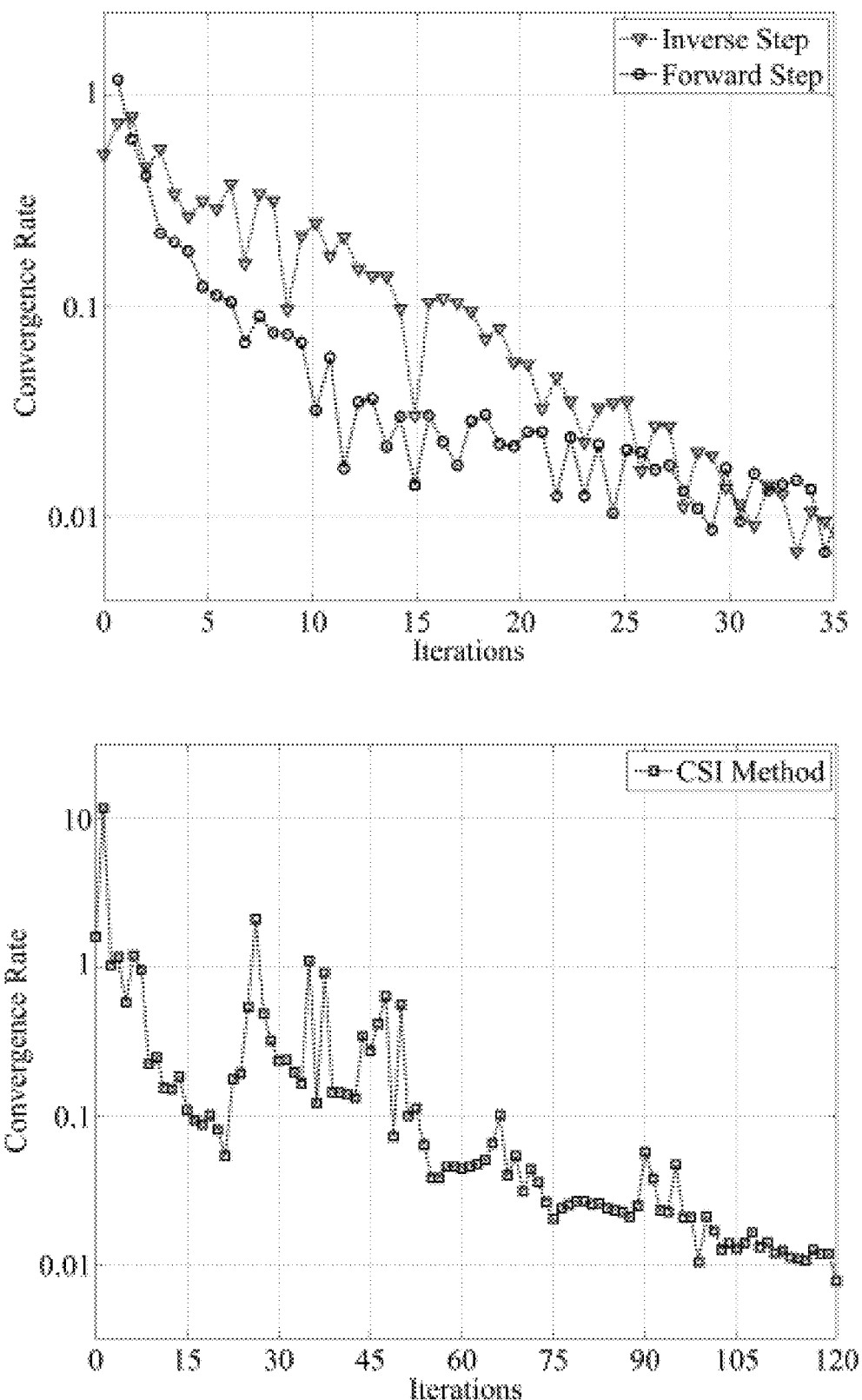
FIG. 13 includes graphs illustrating the convergence of: (a) the differential process described herein (upper graph, with forward and inverse steps shown separately), and (b) the CSI method (lower graph) for the head model of FIG. 12.

The convergence rates for the differential process and the CSI method depicted in FIG. 13 reveal that the differential process requires only 29% of the iterations required by CSI to give the correct solution. The forward and inverse solvers require 10 and 8 seconds, respectively, to complete each iteration. In total, 630 seconds is required to reconstruct the image. In the CSI, 11 seconds is required to complete each iteration step. In total, 1320 seconds is required to reconstruct the image. These results indicate that the differential process is faster by more than twice the equation (5) under CSI optimization.

Figure 14:
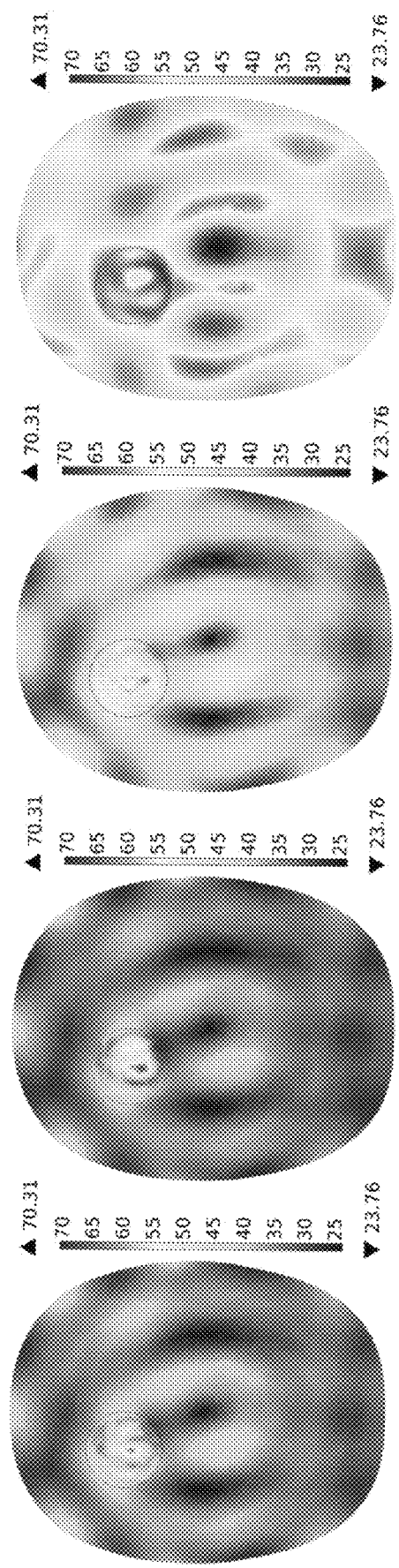
FIG. 14 includes four reconstructed images showing the two-dimensional spatial distribution of relative permittivity $\varepsilon_r$ in plan view slices through the head model of FIG. 12: the three leftmost images were generated by the differential process for slices at z=14, 16, and 15 cm, respectively, whereas the rightmost image was generated by the CSI method for a slice at z=15 cm.
Figure 15:
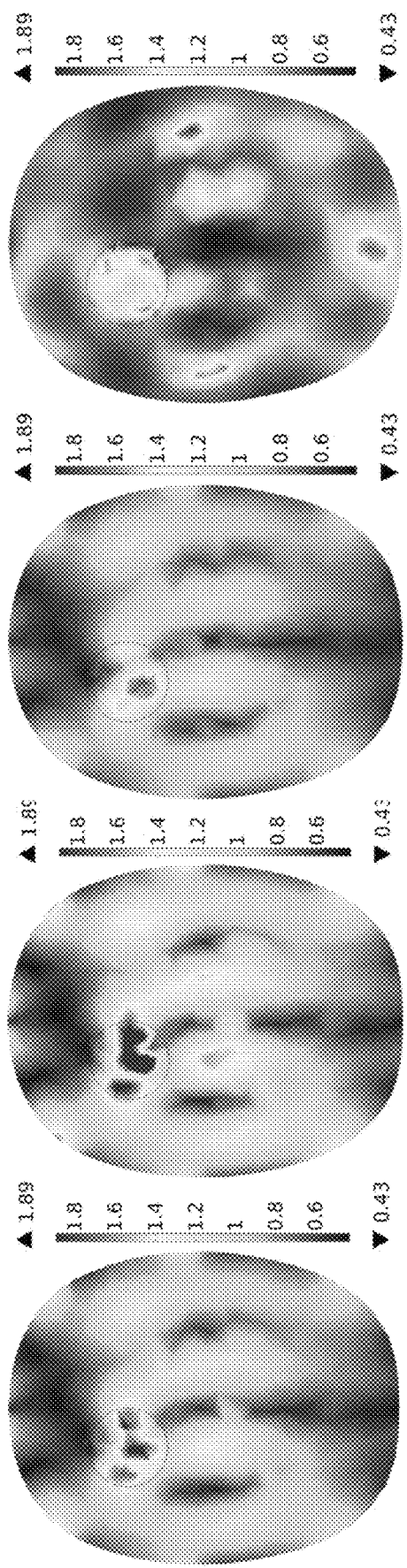
FIG. 15 corresponds to the images of FIG. 14, but showing the two-dimensional spatial distribution of conductivity σ rather than relative permittivity.

FIGS. 14 and 15 show the reconstructed images as a coarse distribution of the tissues, including the bleeding, boundary of the brain, and corpus callosum (central region of the head). The FEM mesh setting used for this problem is: Number of vertex elements: 184, number of edge elements: 1602, number of boundary elements: 6012, number of domain elements: 321387. It is noted from FIG. 15(d) that the conductivity reconstructed by Equation (5) under CSI optimization is rather poor, as the result of ignoring the voltaic integral term.

As discussed above, the diffraction effect is an intrinsic source of non-uniqueness in microwave tomography. This effect results in the resonance-like pattern in the reconstructed images, originating from the nonlinear phase delay and amplitude attenuation. Those nonlinear variations result in what is known as the "echo" effect in Chew. As long as fast imaging is the priority (say in medical emergencies), since the determination of the target is the only crucial requirement, the presence of the echo effect does not possess high medical importance. However, in non-emergency cases, to reduce this effect multi-frequency tomography (with high computational time) can be utilized, followed by echo filters that are frequency gated (as described on page 513 of Chew).

Table I summarizes the computational times and localization errors of the two examples, when the element discretization is quadratic, and single experiment (one simultaneous illumination, discussed in Appendix) for the differential process is performed. For integral-based methods, standard multiple experiments are performed as adding each set of measurements will significantly confine the space of possible solutions during CSI optimization. However, as the number of knowns and unknowns are equal in the linear differential process, the space of possible solutions is not affected by either the successive or simultaneous illumination. The accuracy is defined by the following dimensionless localization error based on the reconstructed dielectric properties:

$$\text{error} = \frac{\sum_{m=1}^{M} |\varepsilon_{exact}^m - \varepsilon_{reconstructed}^m|}{\sum_{m=1}^{M} |\varepsilon_{exact}^m|} \tag{12}$$

where m is the element number in FEM and M is the total number of elements. As seen in Table I, the integral-based method supplemented by CSI is less accurate due to the approximations utilized to reduce equation (4) to equation (5). Moreover, as the relative permittivity of the tumour is around 70 at 1.6 GHz, inspecting FIG. 14 (c) and (d) reveals that, despite the bleeding, CSI has resulted in a false-positive detection of a tumour.

Since the second example is more realistic, the effect of the influential factors on the

TABLE I

THE QUANTITATIVE ANALYSIS FOR TOMOGRAPHY PROBLEMS IN SECTION IV

| Method | Homogeneous Head (time, error) | Heterogeneous Head (time, error) |
|---|---|---|
| Proposed | 110 sec, 0.022 | 630 sec, 0.030 |
| CSI | 580 sec, 0.035 | 1320 sec, 0.185 |

The simulations in COMSOL Multiphysics include quadratic tetrahedral elements for the proposed method when SNR = 20 dB.

computational time and accuracy of the differential process is studied in detail below. It will be shown that for any specific application (either medical on-site emergency, or off-site non-emergency application), a compromise between different influential factors can be made to have an optimum efficiency and accuracy.

A. Effect of Initial Value

Figure 16:
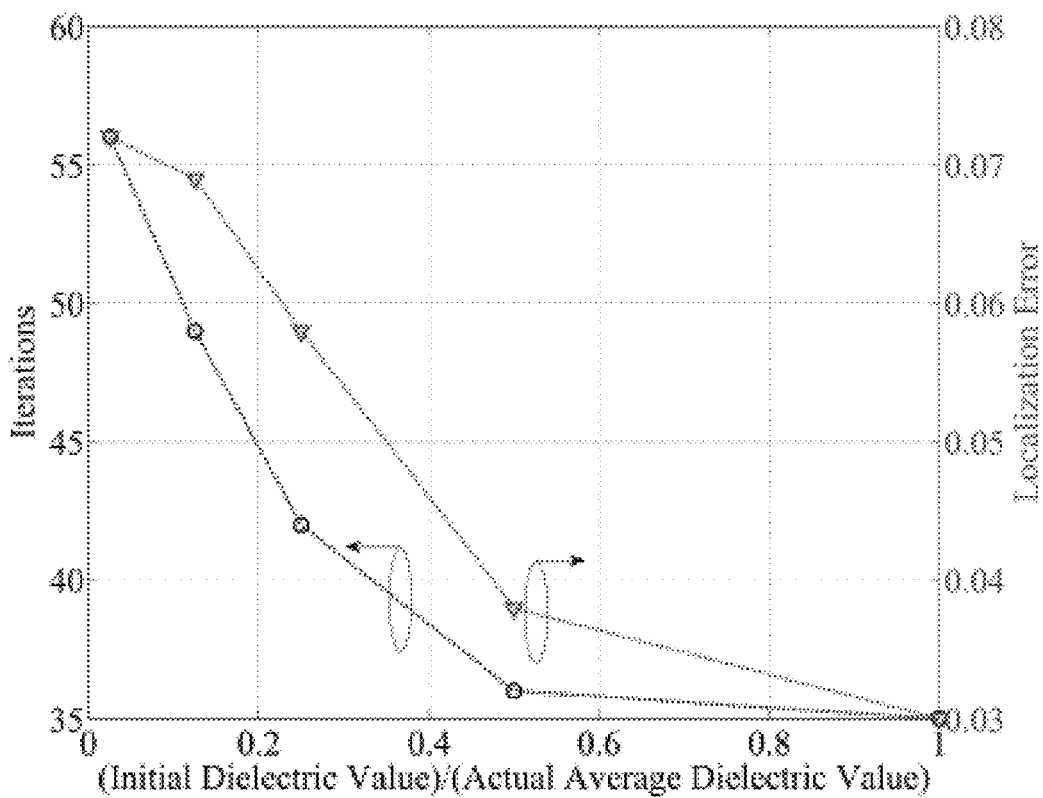
FIGS. 16 to 21 are graphs illustrating the effects of various influential factors on the accuracy and computation time of the differential process described herein.

In the image reconstruction process, an initial value for the dielectric properties of the domain is needed. FIG. 16 shows the effect of that value on the computation time. A proper initial value significantly reduces the computational time by reducing the number of iterations, together with improving the accuracy of the results. When the initial value becomes closer to the actual average value, the solver converges quite quickly. In biomedical applications, that value is well-known as the dielectric properties of tissues do not change significantly from one individual to another. In this example, the other settings are: M=329185, SNR=20 dB, element discretization is quadratic, and single-experiment is performed (8 antennas simultaneously illuminate the domain). Moreover, well-conditioning techniques are applied in all the simulations to make the solver robust with respect to noise.

B. Effect of Noise

Figure 17:
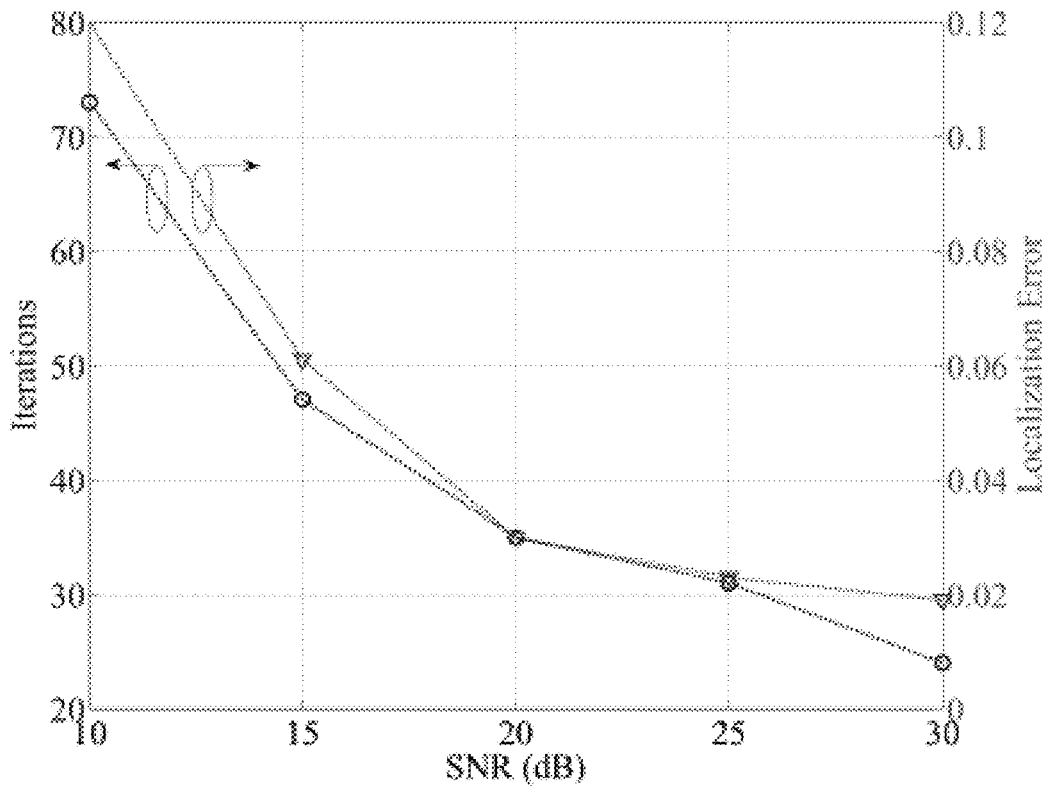

To study the effect of noise, the measured S-parameters are contaminated by random additive noise, ranging from SNR=10 dB, to SNR=30 dB, when M=329185, element discretization is quadratic, and single-experiment is performed. As FIG. 17 illustrates, the effect of noise is significant on the accuracy and computational time. At low SNRs, more iterations are required to reach a specific error degree. Also, the accuracy of the reconstructed image for low SNR is worse than the images obtained at higher SNRs. This result can be explained by the fact that well-conditioning algorithms are able to reduce the noise sensitivity of the FEM solver up to a specific level. Moreover, high noise level (at low SNR) may reach and exceed the signal level of the evanescent waves. Thus, the abrupt changes in the dielectric properties which give rise to the evanescent waves, are no longer detectable.

C. Effect of Element Density

Figure 18:
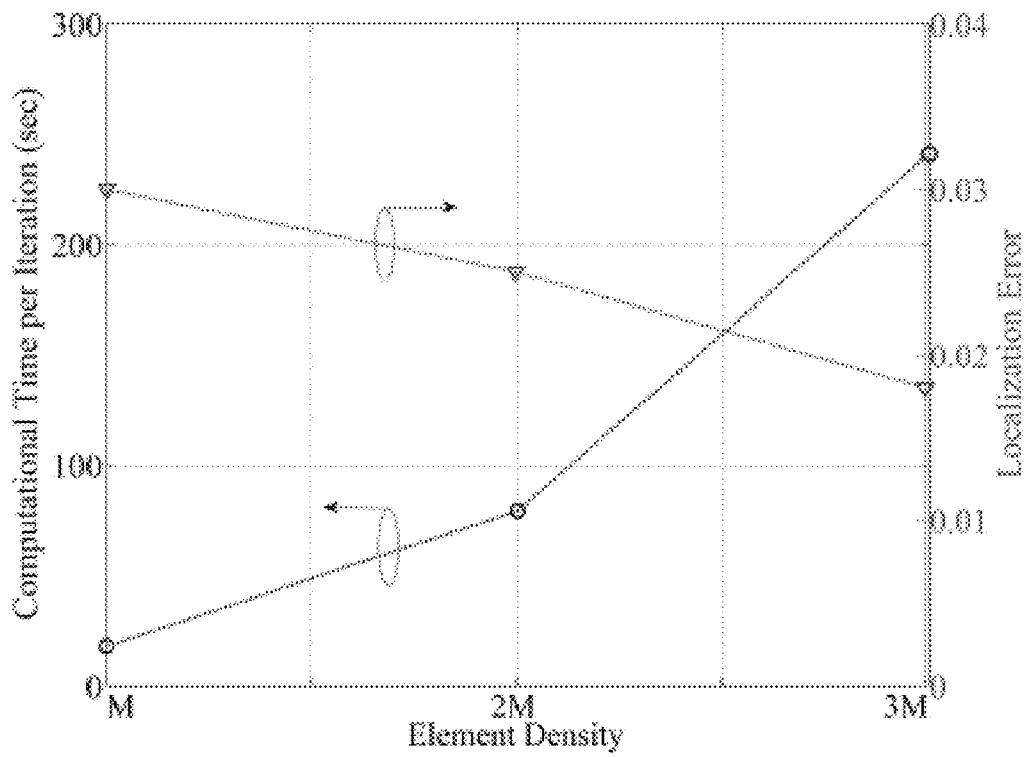

In this subsection, the effect of the density of the adaptive meshes on the computational time and accuracy of the reconstructed image is discussed. In this example, the following parameters are assumed: SNR=20 dB, element discretization is quadratic, and single-experiment is performed. As FIG. 18 shows, increasing the number of meshes (M) significantly increases the computational time of each iteration as the relation between the matrix computational complexity (here FEM stiffness matrix) and its size is nonlinear. Solving a larger matrix equation at each iteration requires much larger computation time. The accuracy of the result, however, is improved, though this improvement is minor and does not worth sacrificing the computational time in medical emergency applications. The reason for this minor improvement is that smaller elements are more accurately able to model the structure of the imaged object. The total number of iterations slightly decreases from 35, for mesh density M, to 29 for mesh density 3M.

D. Effect of Element Discretization

Figure 19:
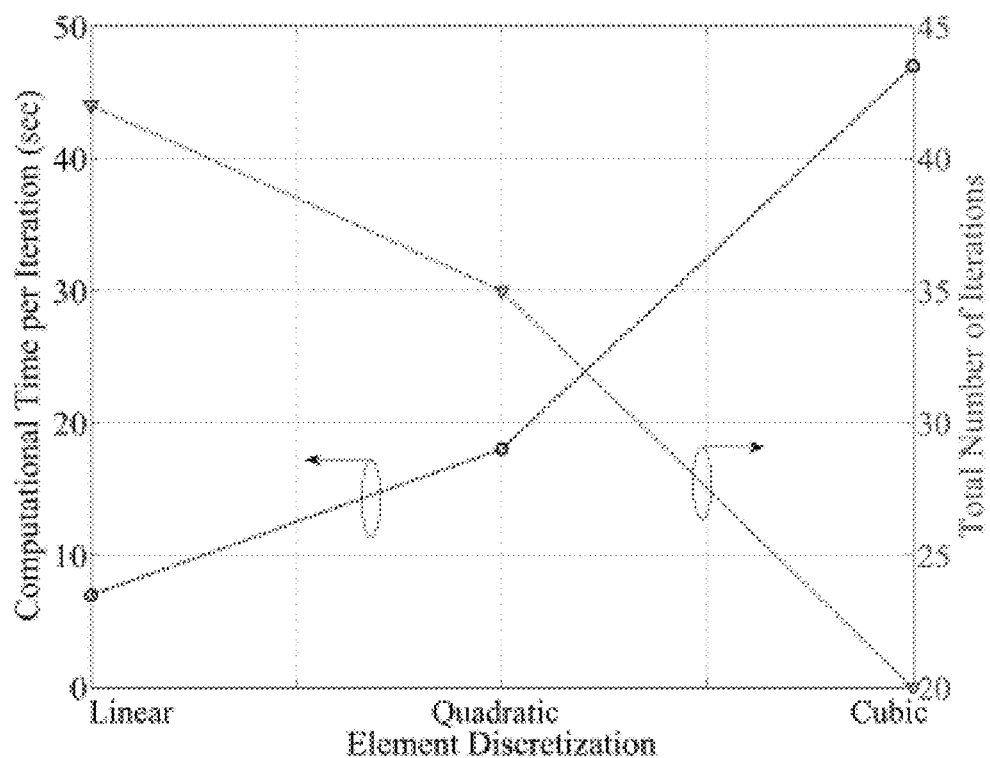
Figure 20:
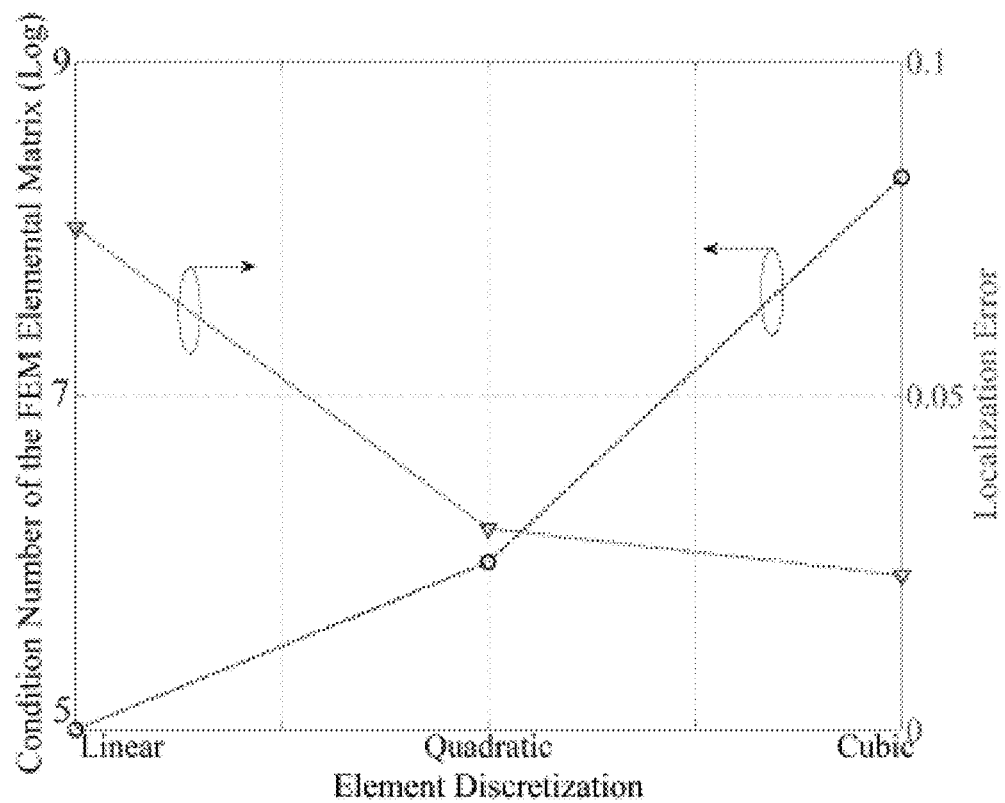

When SNR=20 dB, and single-experiment is performed, implementing the higher order element discretization (cubic) reduces the localization error as seen in FIGS. 19 and 20. However, it increases the computational time per each iteration. The reason for the increased computation time is the increase in the size of the FEM stiffness matrix, which has the same effect when increasing the mesh density, as discussed above. The reason for the accuracy improvement comes from the fact that higher order of nonlinearity in the FEM approximation functions provides better capability for the approximation function to follow the abrupt changes of the unknown function (i.e. the electric field in the forward step, and the permittivity in the inverse step). These abrupt changes are either in the structure of the domain, or in the value of the permittivity. An interesting compromise can be found between the computational time per each iteration, and the total number of iterations. While higher order discretization (cubic) significantly increases the computational time per each iteration, it also noticeably decreases the total number of iterations. This, as discussed, comes from the better ability of the solver to follow the abrupt changes of the electric field and permittivity.

The last point to consider is the effect of the higher order elements on the condition number of the FEM stiffness matrix. The FEM stiffness matrix is ill-conditioned, if one or more pairs of its rows or columns are almost linearly dependent. In other words, the condition number of the FEM stiffness matrix is very high. This happens when one or more pairs of domain elements do not have sufficient connectivity with the rest of the domain. In the proposed method, this problem exists between the elements constructing the antennas with respect to the internal domain of the imaged object (the head), as we do not utilize any matching medium to increase this connectivity. When the element discretization is linear, it utilizes smaller number of elements; thus, less pairs of elements face the insufficient connectivity, and the corresponding condition number is not usually very large. Increasing the approximation order of the FEM increases the number of insufficiently-connected element pairs in the problem domain, and thus significantly increases the condition number. This effect is seen in FIG. 20 for the forward step of the differential process. The condition number of the inverse step is usually at the same order. Fortunately, in either linear, quadratic, or cubic discretization, pivoting or preconditioning algorithms can be used to cope with the ill-conditioning problem. For the cubic discretization, the improvement in localization error is minor, as well-conditioning algorithms can improve the condition number of a matrix up to a specific level. Therefore, since the condition number of some problems may be larger than FIG. 20, using cubic elements may deteriorate the reconstructed dielectric properties.

E. Effect of the Number of Antennas

Figure 21:
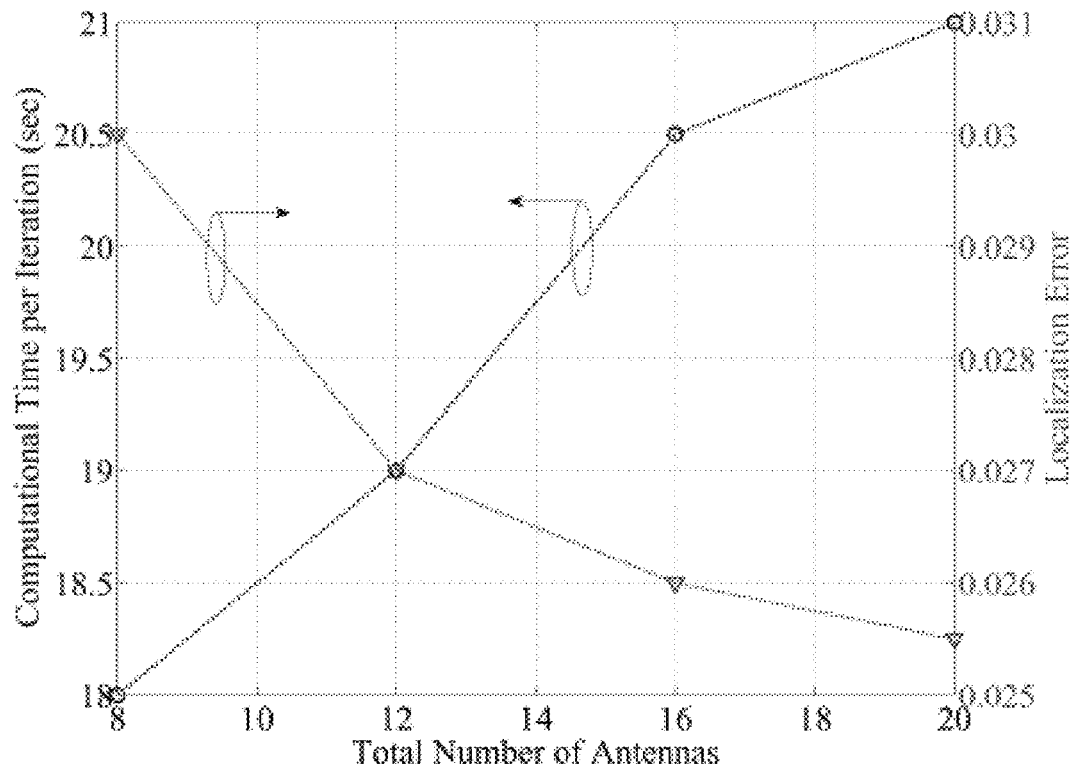

This example uses the simplest type of antenna i.e. the single-resonance thin dipole antenna to image the objects. For this specific antenna, by increasing the number of antennas from 8 to 20, the localization error is reduced. However, this improvement gradually reaches its threshold as seen in FIG. 21 complying the DOF (when M=329185, SNR=20 dB, and element discretization is quadratic). In this study, the total number of iterations is slightly reduced from 35 for 8 antennas to 31 for 20 antennas, as a result of having more measurements (boundary conditions) to support the convergence of the solver. The slight increase in the computational time of each iteration is due to the fact that adding each antenna slightly increases the number of elements, and thus slightly increases the size of the FEM stiffness matrix.

F. Sparsity of the FEM Equations

While sparsity is usually considered in integral-based inverse scattering problems, it can also be adopted in the differential process. Sparsity in EM inverse scattering, by definition, is the representation of the permittivity or electric field (unknown functions) by a linear expansion of the sparse basis functions. Then, the desire is to solve the corresponding linear system of equations formed by the above expansion. As the number of given data is less than the number of unknown data in the integral-based equations, to solve the above linear system of equations, sparsity-based regularization is utilized to cope with the ill-posedness of the problem. Then, the solution is found through an optimization approach reducing the error between the S-parameters derived from measurement and simulation. An important advantage of the sparsity-based techniques is that they result in a sparse system of equations with many zero elements, and this significantly accelerates the calculation process of the inverse problem.

Likewise, in FEM the unknown function (say permittivity or electric field) is firstly represented by a linear expansion of sparse functions (which are zero out of their corresponding element). Then, the variational principle forms the functional of the corresponding partial differential equations of the problem. Following this, as per Ritz's or Galerkin's method, the functional is linearly minimized to find the solution through a sparse system of equations. In this sense, the concept of sparsity is exploited in FEM as well. The difference between FEM and the sparsity-based methods, however, is in the number of known and unknown data. In the sparsity-based methods, as the above numbers are not equal, regularization is used to solve the system of equations through an optimization process. In the proposed approach based on FEM, on the other hand, no sparsity-based regularization is necessary (while still utilizable) as the above numbers are equal and the system of equations is linear, yielding the solution by a direct inversion step $[x]_{M \times 1} = [A]_{M \times M'}^{-1} [b]_{M' \times 1}$.

G. Attainable Accuracy

In non-emergency scenarios where time does not possess a critical importance, it is usually of special interest to evaluate the best attainable accuracy by a proposed method within a specific example. To this end, and according to the effect of different factors on the accuracy of the proposed method shown in FIGS. 16 to 21, the following settings lead us to attain the final accuracy for the single-frequency problem in FIG. 12: 1) An initial value around $\varepsilon_r = 42$ and $\sigma = 1.17$, 2) SNR=25 dB (assuming that higher SNR is not achievable in real scenarios), 3) 20 number of dipole antennas which meet the DOF 4) Quadratic element discretization, 5) Adaptive meshing (which defines the best mesh configuration as per the computer specifications). These settings result in a localization error of 0.018. In this optimum setting, the convergence plots for the forward and inverse steps of the differential process reach 0.0067 and 0.0078, respectively. Solving the problem using CSI with the above parameters (excluding 4 and 5 that are not applicable) results in a localization error of 0.112, and the achievable convergence 0.0045. The better convergence of CSI, however, merely represents the best attainable solution by CSI. Due to the larger space of possible solutions in CSI, its better convergence does not necessarily indicate that the converged CSI solution is more accurate than the differential process.

Integral-based EM medical tomography suffers from serious limitations that confine the problem to 2D imaging and require the imaging antennas to be modelled as point sources, and to assume homogeneity along one spatial coordinate axis. These limitations and approximations are associated with the 3D Green's function, which is not derivable or is computationally extensive under the integral operator. The proposed differential equations for EM medical tomography provide, for the first time, the possibility of solving this class of problems via well-known numerical techniques, like FEM, which are not based on the Greens function. Consequently, 3D accurate images can be rapidly reconstructed, without any of the usual approximations of considering the antennas as point sources or assuming homogeneity of the domain along one coordinate axis. This rapid and accurate image reconstruction process plays a key role in emergency medical scenarios, such as professional sports or road accidents for example, where having a true initial understanding of injuries at early stages can remarkably improve the chance of survival.

APPENDIX I

Deriving the Boundary Conditions from S-Parameters

Figure 22:
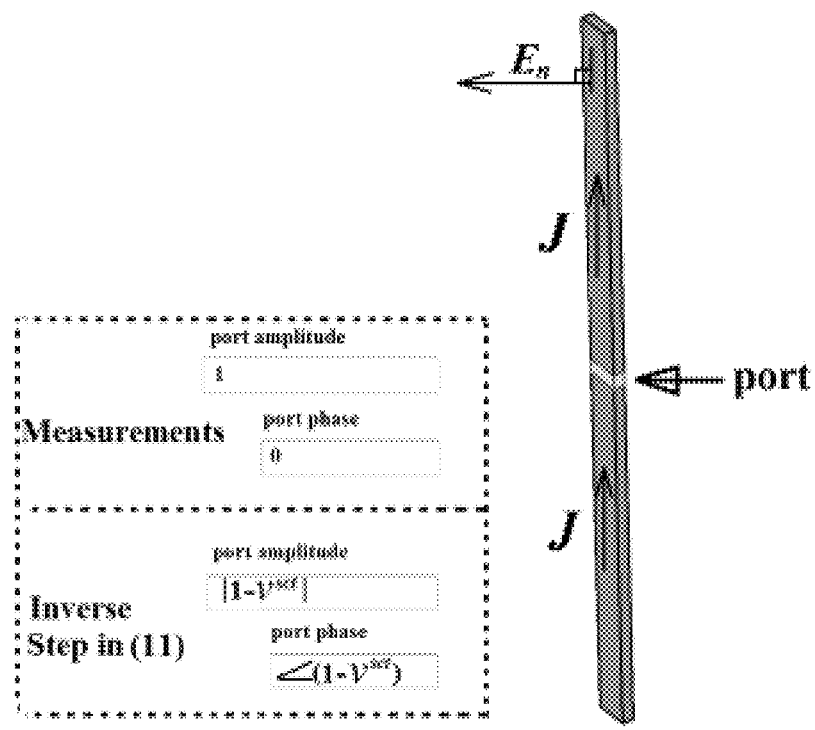
FIG. 22 illustrates the procedure of exciting the antennas in the inverse step of the differential process to derive suitable boundary conditions.
Figure 23:
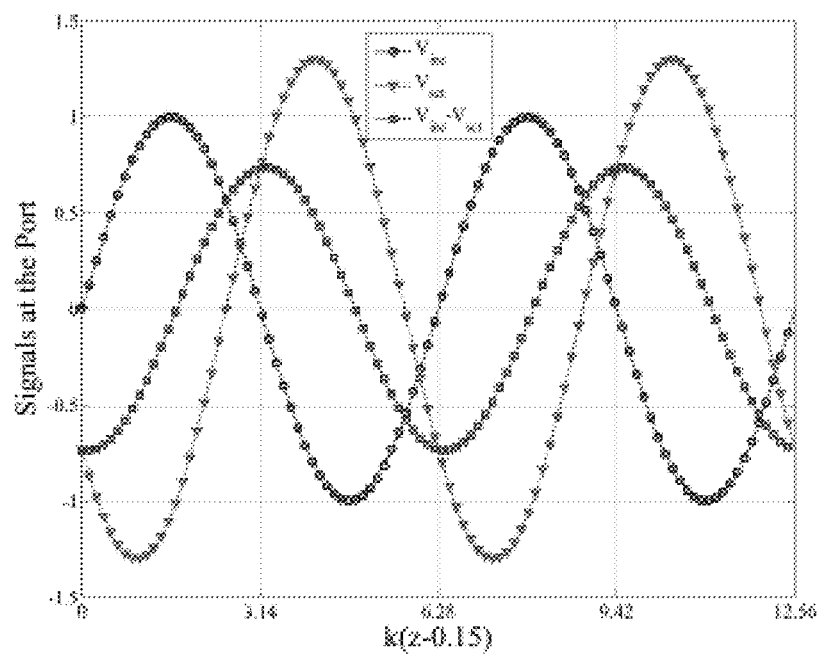
FIG. 23 is a graph showing typical different voltage signals at the port of the antenna of FIG. 22.

This appendix describes the procedure of deriving the normal component of the electric field $\vec{E}_n$ (the tangential component is almost zero for good conductors like copper), and the current density $\vec{J}$ on the antenna conductors, from measured S-parameters. FIGS. 22 and 23 show a thin dipole antenna used for imaging, its port where the S-parameters are recorded, and the port excitations in each measurement.

The antennas can be excited simultaneously, or sequentially. A first approach requires a number of synchronized transceivers that is equal to the number of imaging antennas, whereas a second approach requires one transceiver, and is the standard measurement approach. This appendix explains in detail how the data recorded by the standard approach through multi-static illumination through measurements can be combined to give simultaneous illumination in the image reconstruction process.

In the measurements, the port of each antenna (say the $i^{th}$ antenna) is excited by a specific voltage, say $v_i^{inc}$, while all other antenna ports are kept in a matched condition. This voltage then forms a charge (and thus a current) on the $i^{th}$ antenna's conductive face. As per the electromagnetic boundary conditions, this charge forms the normal component of the electric field over that conductive face, as defined in Equation (1), while the tangential component of the electric field is clearly zero. This field then propagates into the domain, and after multi-scatterings, specific portions of the scattered electric field is incident upon the conductive surface of each antenna, say the $j^{th}$ antenna, of the imaging array. This portion of the electric field, in turn, applies a charge (and thus, a current) on the $j^{th}$ antenna conductive surface, and correspondingly, a voltage, say $v_j^{sct}$, at its port. As per the standard definition, the ratio of the two voltages, $v_j^{sct}$ and $v_i^{inc}$, is the S-parameter $S_{ji}$, which is defined as $$S_{ji} = \frac{v_j^{sct}}{v_i^{inc}} \tag{A1}$$

The above relation can be rewritten in a more general form for all the antennas' ports (N is the number of antennas) as:

$$\begin{bmatrix} v_1^{sct} \\ v_2^{sct} \\ \vdots \\ v_N^{sct} \end{bmatrix} = \begin{bmatrix} S_{11} & S_{12} & \cdots & S_{1N} \\ S_{21} & S_{22} & \cdots & S_{2N} \\ \vdots & \vdots & \ddots & \vdots \\ S_{N1} & S_{N2} & \cdots & S_{NN} \end{bmatrix} \begin{bmatrix} v_1^{inc} \\ v_2^{inc} \\ \vdots \\ v_N^{inc} \end{bmatrix} \tag{A2}$$

In other words, when the antennas are sequentially excited by equal normalized (without loss of generality) voltage of $v_i^{inc} = 1^{\angle 0}$, the following relation holds:

$$\begin{bmatrix} v_1^{sct} \\ v_2^{sct} \\ \vdots \\ v_N^{sct} \end{bmatrix} = \begin{bmatrix} S_{11} & S_{12} & \cdots & S_{1N} \\ S_{21} & S_{22} & \cdots & S_{2N} \\ \vdots & \vdots & \ddots & \vdots \\ S_{N1} & S_{N2} & \cdots & S_{NN} \end{bmatrix} \begin{bmatrix} 1^{\angle 0} \\ 1^{\angle 0} \\ \vdots \\ 1^{\angle 0} \end{bmatrix} \tag{A3}$$

In practice, this can be easily realized using any vector network analyzer or transceiver with a controlled reference signal. With some simple manipulations:

$$v_1^{sct} = \sum_{i=1}^{N} S_{1i} \quad (A4)$$

$$v_2^{sct} = \sum_{i=1}^{N} S_{2i}$$

$$\vdots$$

$$v_N^{sct} = \sum_{i=1}^{N} S_{Ni}$$

Hence, the combined scattered voltage at each antenna, after completing the successive measurements, is the superposition of the individual scattered voltages. It is the same voltage if simultaneous illumination is used. This total voltage in Equations (A4) thus corresponds to the total current density and electric field on each antenna's conductive face due to the scattering effects. It does not include the incident voltage. It is noted that the surface charge density is identical to the normal component of the electric field (multiplied by $\varepsilon_0$), and the same relation is valid between the surface current density and the tangential component of the magnetic field. Hence, there is no need to directly calculate the charge and current densities, as deriving the electromagnetic fields is sufficient for this purpose.

The total voltage at the antenna port is $$v_i^{inc} + v_i^{sct} = 1^{\angle 0} + \sum_{j=1}^{N} S_{ij},$$

and the total current is $$I_i^{inc} - I_i^{sct} = v_i^{inc} - v_i^{sct} = 1^{\angle 0} - \sum_{j=1}^{N} S_{ij}.$$

Hence, when the port of the $i^{th}$ antenna is excited by $1^{\angle 0} + v_i^{sct}$, or $1^{\angle 0} - v_i^{sct}$, the normal electric field and current density formed on the entire conducting surface of the ith antenna, approximately show the desired $\vec{E}_n$ and $\vec{J}$, as if the antennas are simultaneously illuminating the domain. The minus sign for $-v^{sct}$ in the equation for the electric current (seen in FIG. 22), is needed to satisfy the conservation of charge law (or Kirchhoff's current law in circuit theory). Table A1 below shows the normalized reconstructed electric and magnetic fields at the ports of the 8 dipole antennas shown in FIG. 12, with and without the bleeding region.

TABLE A1

THE NORMALIZED RECONSTRUCTED FELDS AT THE ANTENNA PORTS IN FIG. 12

| Antenna | Without Bleeding $\vec{E}$ (amplitude, phase) $\vec{H}_t$ (amplitude, phase) | With Bleeding $\vec{E}$ (amplitude, phase) $\vec{H}_t$ (amplitude, phase) |
|---|---|---|
| #1 | (180.77, 2.9059) | (174.17, 2.9505) |
|    | (0.6571, 0.1607) | (0.6782, 0.0914) |
| #2 | (131.17, 3.1072) | (125.14, 3.1497) |
|    | (0.9212, −0.1633) | (0.9746, −0.2066) |
| #3 | (150.04, 3.0879) | (151.83, 3.1484) |
|    | (0.4614, −0.2147) | (0.4729, −0.3189) |
| #4 | (109.17, 3.1341) | (118.95, 3.0573) |
|    | (0.2163, 3.0187) | (0.2104, 3.0927) |
| #5 | (164.04, 3.0245) | (155.56, 2.9780) |
|    | (0.6220, 3.1014) | (0.6827, 3.1472) |
| #6 | (174.68, 3.1551) | (180.07, 3.2001) |
|    | (0.9419, 2.9095) | (0.9187, 2.8359) |
| #7 | (163.98, 3.2864) | (170.72, 3.2861) |
|    | (0.5377, 2.7446) | (0.5160, 2.7249) |
| #8 | (174.42, 3.1552) | (174.40, 3.1375) |
|    | (0.2194, −0.1598) | (0.2175, −0.1264) |

The antenna numbers are counted counter-clockwise, starting from the antenna facing the head frontal. The phase unit is radian.

Note that in this approach, when the $i^{th}$ antenna is excited during the reconstruction process of tomography by $1^{\angle 0} + v_i^{sct}$, or $1^{\angle 0} - v_i^{sct}$ for the current, all other antennas and objects are removed from the domain to avoid duplication in considering the already included effects of all other antennas and the image domain. One must be careful, however, that this empty domain is not the image reconstruction domain, but a domain utilized only for approximately reconstructing the fields and currents on the antennas. The derived $\vec{E}_n$ and $\vec{J}$ are then inserted in Equation (11) as boundary conditions for the image reconstruction domain, and remain unchanged during the iterative process of FIG. 2. It is also noted that choosing the current excitation for the port, the actual excitation is $$\frac{1^{\angle 0} - v_i^{sct}}{Z_0},$$

where $Z_0$ is the characteristic impedance of the antenna at its port.

The parameters $v^{inc}$, $v^{sct}$, $v^{inc} - v^{sct}$, $v^{inc} + v^{sct}$ are all single-tone harmonic functions (at 1.6 GHz in the included examples. More precisely, all the EM wave functions like $\vec{E}_n$ and $\vec{J}$ in such a single-frequency time-harmonic regime are well defined by their amplitude and phase at the port. Thus, all these quantities can be scaled with respect to each other by simply multiplying them by a suitable weighting function. The distribution of the electric field and current on the antenna surface, nevertheless, can only be approximately derived, because there are two unavoidable limitations in the reconstructed fields and currents on the antenna surfaces. Firstly, the fields reflected back from the sharp edges and corners of any structure in the problem domain (say, antenna edges) mainly give rise to evanescent waves. These waves decay when propagating. Consequently, they may not have remarkable signature at the port of the antenna, where the scattered signals are recorded as their signal level may be close to the noise level. Secondly, the inductive or capacitive loading effect of the imaged object, which slightly deforms the distribution of the electric field and current on the radiating surface of the antenna, cannot be reconstructed, as the object is generally unknown and the voltage at the port given in FIG. 22 can only reconstruct the amplitude and phase of the electric field and current. Nevertheless, this approach is accurate for wire-like antennas where the current and field distributions are almost one-dimensional, where only amplitude and phase is important across the antenna, and the 2D field and current distributions are negligible. It is worth mentioning that the loading effects of the imaged object on the antennas are usually noticeable when the antenna is very close to the object, and the object is highly conductive. For biomedical applications, where tissues are not highly conductive, only the first case must be taken into account by adjusting the distance of the antenna to minimize the loading effects.

Figure 24:
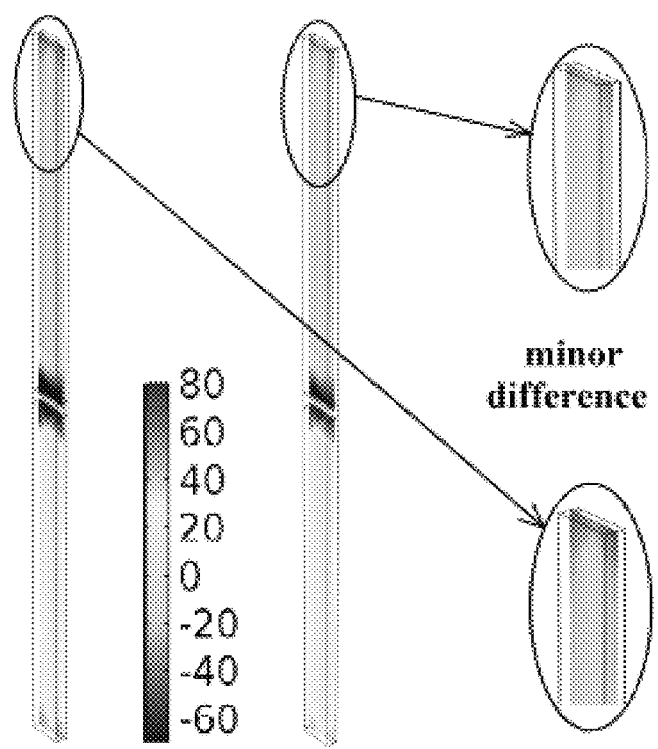
FIGS. 24 and 25 show the distributions of the normal component of the electric field and the current density, respectively, on one of the antennas in FIG. 4f.
Figure 25:
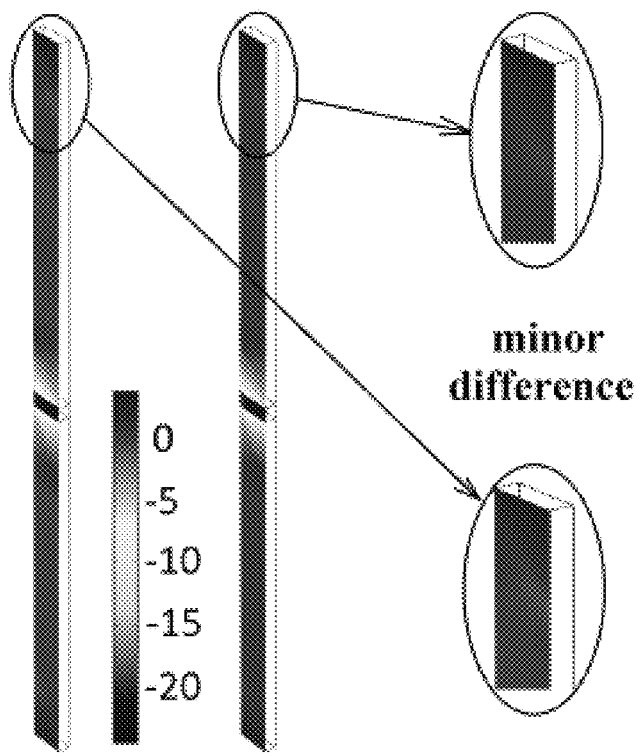
Figure 26:
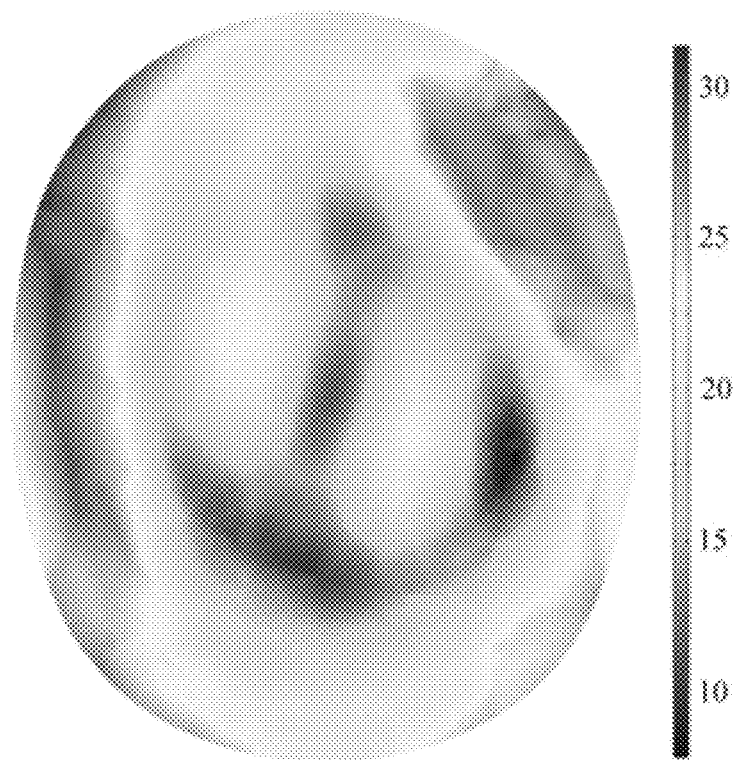
FIGS. 26 and 27 show that the inability to accurately include the evanescent waves means the reconstructed image slice of FIG. 12 crossing the antenna edges, that are far from the antenna port, are not as accurate as those shown in FIGS. 14 and 15 for slices closer to the port.
Figure 27:
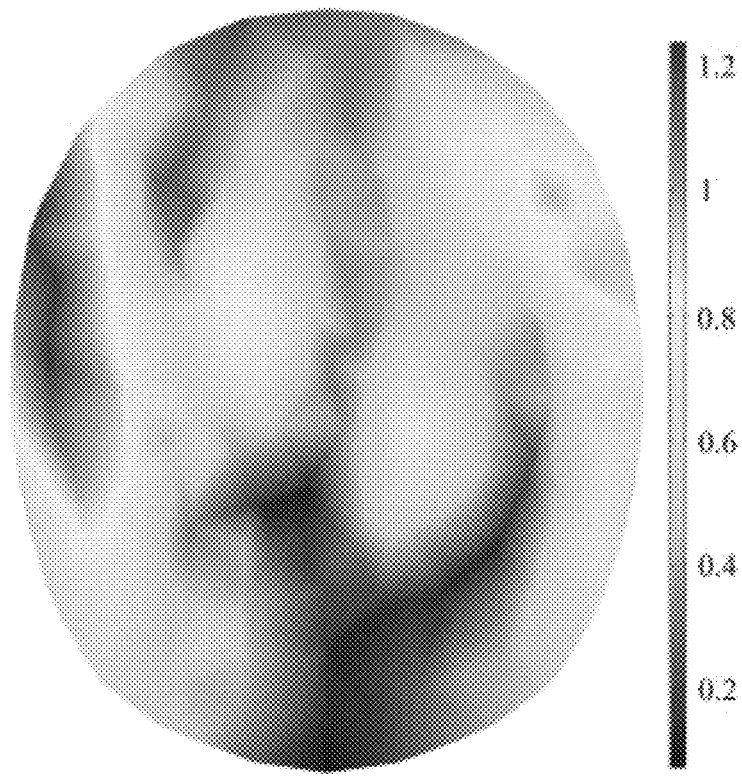
Figure 28:
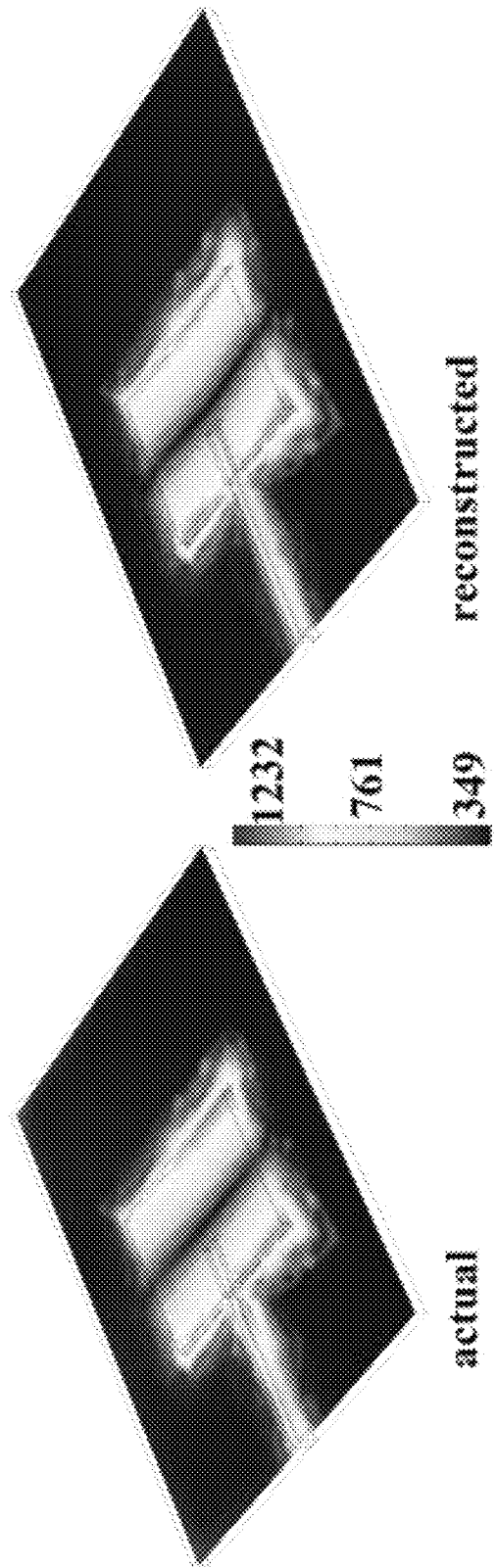
FIG. 28 shows a calculated field distribution in comparison with the actual distribution for patch antennas operating at 1.6 GHz, designed on FR4 with 1.6 mm thickness, to illustrate the impact of the explained limitations on wide planar antennas.

As an example, to see the effects of the above limitations on the explained approach, the distributions of the normal component of the electric field and the current density on one of the antennas in FIG. 4f are shown in FIGS. 24 and 25, respectively, using the explained approach in comparison with the real distributions. As seen, the calculated results are quite close to the actual values. The minor difference in the distributions comes from the rapidly decaying evanescent waves from the antenna edges, which are not reconstructed well enough through this approach. Since the used antenna is wire-like, fields and currents have mainly 1D distributions, and the effect of the second limitation discussed above, is negligible. The inability to accurately include the evanescent waves means the reconstructed image slice of FIG. 12 crossing the antenna edges (FIGS. 26 and 27), that are far from the antenna port, are not as accurate as those shown in FIGS. 14 and 15 for slices closer to the port. To see the impact of the explained limitations on wide planar antennas, the previous investigation is repeated on patch antennas operating at the same frequency (1.6 GHz), designed on FR4 with 1.6 mm thickness). The calculated field distribution is shown in FIG. 28 in comparison with the actual distribution. The reconstructed distribution is close to the actual one, but a slight deformation on the field distribution, mainly at the centre of the antenna, is seen in the actual case, which is not reconstructed by the process described herein. In comparison with existing 2D methods, which utilize the scattered field at only one point to reconstruct the fields and dielectric properties of the imaged object, the described process reconstructs, reasonably well, the scattered field and current over the entire structure of the antenna. The described process thus provides additional valuable information to the imaging process, and significantly improves tomography, especially for fast biomedical imaging.

Many modifications will be apparent to those skilled in the art without departing from the scope of the present invention.

The invention claimed is:

1. A tomographic imaging process, including: accessing scattering parameter data representing electromagnetic waves scattered by features within an object and originating from a plurality of antennas disposed around the object on a boundary S; processing the scattering parameter data to generate a reconstructed image representing a spatial distribution of features within the object, said processing including: solving an electromagnetic inverse problem, wherein forward and inverse steps of the inverse problem are represented and solved as respective differential equations involving an electric field to determine values for the electric field; and processing the determined values of the electric field to generate reconstructed image data representing one or more spatial distributions of one or more electromagnetic properties within the object, wherein processing the scattering parameter data includes estimating permittivity values of the object by processing the scattering parameter data of the object and pre-determined training data for a plurality of different scattering media, and wherein the pre-determined training data includes regression coefficients representing a quadratic relationship between a function of scattering parameters for scattering by different training scattering media having respective different permittivity values and said respective different permittivity values.

2. The process of claim 1, wherein the inverse step is represented by a differential equation and boundary conditions (BC) of the form:

$$(\nabla \cdot E)\varepsilon + E \cdot \nabla \varepsilon = 0$$

$$BC: \begin{cases} \varepsilon = \dfrac{\rho_s + \varepsilon_2 E_{2n}}{E_{1n}} \text{(on the imaging antennas)} \\ \varepsilon = \dfrac{\mu_0 (H_t)^2}{\omega^2 (E_{t'})^2} = \dfrac{\mu_0 (H_{t'})^2}{\omega^2 (E_t)^2} \text{ (on } S\text{)} \end{cases}$$

where $E_{1n}$ and $E_{2n}$ are the two normal components of the electric fields on both sides of the boundary S derived from the scattered field $E_n^{sct}$ recorded on S and the incident field $E_n^{inc}$ as $E_n = E_n^{inc} + E_n^{sct}$.

3. The process of claim 1, wherein the forward step is represented by a differential equation and boundary conditions (BC) of the form:

$$\nabla \times \nabla \times E - k^2 E = 0$$

$$BC: \begin{cases} n \times (E_1 - E_2) = 0 \\ n \cdot (\varepsilon_1 E_1 - \varepsilon_2 E_2) = \rho_s \\ n' \times \nabla \times E - jkn' \times E \times n' = 0 \text{ (absorbing } BC\text{)} \end{cases}$$

4. The process of claim 1, wherein the function of scattering parameters is a variogram according to:

$$\gamma_i(h) = \dfrac{1}{2|N(h)|} \sum_{(j,k) \in N(h)} |S_{ij} - S_{ik}|^2$$

where h is the distance between the $j^{th}$ and $k^{th}$ transmitting antenna locations, $S_{ij}$ is the received signal at the $j^{th}$ antenna transmitted from the $j^{th}$ antenna using $N_f$ frequency samples, and N(h) denotes the set of pairs of observations ij and ik such that $|r_{ij} - r_{ik}| = h$ and $|N(h)|$ is the number of pairs in the set; and the step of estimating the permittivity values of the object includes generating a corresponding variogram from the scattering parameter data of the object.

5. The process of claim 4, including representing an effective permittivity from the view point of ith receiver as:
where $s = \{\gamma, h\}$, $f(s) = [1, \gamma, h, \gamma^2, \gamma h, h\gamma, h^2]$ is a quadratic regression function vector, and w is a 7×1 vector of regression coefficients to be calculated for a minimized error z(s).

6. The process of claim 1, including energizing the plurality of antennas disposed about the object to cause the antennas to radiate electromagnetic waves onto the object.

7. The process of claim 1, including detecting the electromagnetic waves scattered by the features within the object, and generating the scattering parameter data based on said detecting.

8. The process of claim 7, wherein the electromagnetic waves scattered by the features within the object are detected by the antennas.

9. A tomographic imaging process, including:
accessing scattering parameter data representing electromagnetic waves scattered by features within an object and originating from a plurality of antennas disposed around the object on a boundary S;
processing the scattering parameter data to generate a reconstructed image representing a spatial distribution of features within the object, said processing including: solving an electromagnetic inverse problem, wherein forward and inverse steps of the inverse problem are represented and solved as respective differential equations involving an electric field to determine values for the electric field; and
processing the determined values of the electric field to generate reconstructed image data representing one or more spatial distributions of one or more electromagnetic properties within the object, the process further including determining a boundary of the object prior to processing the scattering parameter data, wherein the reconstructed image is generated on the basis of the determined boundary of the object, wherein the boundary of the object is determined from a relation between distances of the object from the antenna and corresponding reflection coefficients.

10. The process of claim 9, including determining a relation between distances of the object from the antenna and respective resonant frequencies, wherein the boundary is determined on the basis of the relation.

11. The process of claim 9, including using a vector network analyser port calibration method to determine a relation between distances of the object from the antenna and respective measurements of a scattering parameter $S_{11}$, wherein the boundary is determined on the basis of the relation.

12. The process of claim 9, including determining a relation between distances of the object from the antenna and input impedances of the antenna, wherein the boundary is determined on the basis of the relation.

13. The process of claim 9, including measuring frequency domain reflection coefficients around the object and using a frequency to time domain transform to convert the frequency domain measurements to time domain measurements, and using the geometry of the antenna to map the time domain measurements to a spatial domain to determine the boundary of the object.

14. A computer-readable storage medium having stored thereon processor-executable instructions that, when executed by at least one processor of a data processing system, cause the at least one processor to execute the process of claim 1.

15. A tomographic imaging system, including a data processing component having a memory and at least one processor configured to:
access scattering parameter data representing electromagnetic waves scattered by features within an object and originating from a plurality of antennas disposed around the object on a boundary S;
process the scattering parameter data to generate a reconstructed image representing a spatial distribution of features within the object, said processing including:
solving an electromagnetic inverse problem, wherein forward and inverse steps of the inverse problem are represented and solved as respective differential equations involving an electric field to determine values for the electric field; and
process the determined values of the electric field to generate reconstructed image data representing one or more spatial distributions of one or more electromagnetic properties within the object,
wherein processing the scattering parameter data includes estimating permittivity values of the object by processing the scattering parameter data of the object and pre-determined training data for a plurality of different scattering media, and
wherein the pre-determined training data includes regression coefficients representing a quadratic relationship between a function of scattering parameters for scattering by different training scattering media having respective different permittivity values and said respective different permittivity values.

16. The system of claim 15, wherein the inverse step is represented by a differential equation and boundary conditions (BC) of the form:

$$(\nabla \cdot E)\varepsilon + E \cdot \nabla \varepsilon = 0$$

$$BC : \begin{cases} \varepsilon = \dfrac{\rho_s + \varepsilon_2 E_{2n}}{E_{1n}} \text{ (on the imaging antennas)} \\ \varepsilon = \dfrac{\mu_0 (H_t)^2}{\omega^2 (E_{t'})^2} = \dfrac{\mu_0 (H_{t'})^2}{\omega^2 (E_t)^2} \text{ (on } S) \end{cases}$$

where $E_{1n}$ and $E_{2n}$ are the two normal components of the electric fields on both sides of the boundary S derived from the scattered field $E_n^{sct}$ recorded on S and the incident field $E_n^{inc}$ as $E_n = E_n^{inc} + E_n^{sct}$.

17. The system of claim 15, wherein the forward step is represented by a differential equation and boundary conditions (BC) of the form:

$$\nabla \times \nabla \times E - k^2 E = 0$$

$$BC : \begin{cases} n \times (E_1 - E_2) = 0 \\ n \cdot (\varepsilon_1 E_1 - \varepsilon_2 E_2) = \rho_s \\ n' \times \nabla \times E - jkn' \times E \times n' = 0 \text{ (absorbing } BC) \end{cases}$$

18. The system of claim 15, wherein the at least one processor is further configured to cause the plurality of antennas disposed about the object to radiate electromagnetic waves onto the object.

* * * * *